(12) United States Patent
Chen et al.

(10) Patent No.: US 11,280,867 B2
(45) Date of Patent: Mar. 22, 2022

(54) SYSTEM AND METHOD FOR QUANTITATIVE MAGNETIZATION TRANSFER IMAGING BASED ON SPIN-LOCK

(71) Applicant: The Chinese University of Hong Kong, Hong Kong (CN)

(72) Inventors: Weitian Chen, Hong Kong (CN); Jian Hou, Xincheng Township, Xiangfen County (CN); Baiyan Jiang, Jakarta (ID)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 15/929,627

(22) Filed: May 13, 2020

(65) Prior Publication Data

US 2021/0141041 A1    May 13, 2021

Related U.S. Application Data

(60) Provisional application No. 62/933,187, filed on Nov. 8, 2019.

(51) Int. Cl.
*G01R 33/56* (2006.01)
*A61B 5/055* (2006.01)
*G01R 33/48* (2006.01)
*G01R 33/50* (2006.01)

(52) U.S. Cl.
CPC .......... *G01R 33/5605* (2013.01); *A61B 5/055* (2013.01); *G01R 33/4828* (2013.01); *G01R 33/50* (2013.01)

(58) Field of Classification Search
CPC ........................ G01R 33/5605; G01R 33/4828; G01R 33/50; A61B 5/055
See application file for complete search history.

(56) References Cited

U.S. PATENT DOCUMENTS 5,281,917 A * 1/1994 Santyr ................ G01R 33/4828
324/307

FOREIGN PATENT DOCUMENTS

WO    WO-9010878 A1 * 9/1990 ........... G01R 33/446

OTHER PUBLICATIONS

Jin, et al. "Quantitative chemical exchange sensitive MRI using irradiation with toggling inversion preparation." Magnetic resonance in medicine 68, No. 4 (2012): 1056-1064.
Smith, et al. "Rapid, high-resolution quantitative magnetization transfer MRI of the human spinal cord." NeuroImage 95 (2014): 106-116.
Zaiss, et al. "A combined analytical solution for chemical exchange saturation transfer and semi-solid magnetization transfer." NMR in biomedicine 28, No. 2 (2015): 217-230.

* cited by examiner

*Primary Examiner* — Susan S Lee
(74) *Attorney, Agent, or Firm* — Kilpatrick Townsend & Stockton LLP

(57) ABSTRACT

Systems and methods for fast and robust quantification of magnetization transfer (MT) using off-resonance spin-lock MRI. The techniques can be insensitive to variations of the inherent relaxation rates R1 (1/T1) and R2 (1/T2) of the free-water pool and to variations of the chemical exchange pool. The techniques can also be robust in the presence of inhomogeneity in the B1 RF and/or B0 magnetic fields.

40 Claims, 11 Drawing Sheets
(7 of 11 Drawing Sheet(s) Filed in Color)

SYSTEM AND METHOD FOR QUANTITATIVE MAGNETIZATION TRANSFER IMAGING BASED ON SPIN-LOCK

CROSS-REFERENCE TO RELATED APPLICATION

This application claims the benefit of U.S. Provisional Patent Application No. 62/933,187, filed Nov. 8, 2019, the disclosure of which is incorporated herein by reference in its entirety.

BACKGROUND

This disclosure relates generally to magnetic resonance imaging (MRI) techniques, and in particular to techniques for quantitative magnetization transfer (MT) imaging based on spin-lock.

Magnetic resonance imaging (MRI) is a noninvasive diagnostic technique that can allow assessments of the composition and state of various tissues. In an MRI procedure, a patient is placed in a strong longitudinal magnetic field (B0) that aligns nuclear spins of atoms in the patient's body, producing a net magnetization vector. RF pulses with magnetic field components (B1) transverse to the longitudinal field and frequencies tuned to the Larmor frequency of an isotope of interest (often $^1$H) are applied. These pulses can flip spins into a higher energy state, resulting in a transverse component to the magnetization vector. As these spins return to the ground state, responsive RF pulses from the patient's body can be detected. Based on the response to pulses, characteristics of the magnetization can be measured. Commonly used measurements include the spin-lattice relaxation time (T1), measurement of which is typically based on recovery of the longitudinal component of the magnetization vector, and the spin-spin relaxation time (T2), measurement of which is typically based on decay of the transverse component of the magnetization vector. Since different anatomical structures have different material compositions, quantification of T1 and/or T2 can provide information about the material composition of a structure being imaged, and particular pulse sequences can be optimized to quantify T1 or T2. Spin-lattice relaxation time in the rotating frame, known as $T_{1\rho}$ (or $R_{1\rho}=1/T_{1\rho}$), is a magnetization characteristic that is sensitive to molecular interactions, including dipolar interactions, chemical exchange, and magnetization transfer. $R_{1\rho}$ quantification is typically performed using spin-lock MRI. However, $R_{1\rho}$ relaxation also occurs during off-resonance RF saturation.

In addition to providing high-quality anatomical images of tissues, MRI can be used to examine tissue at a molecular level. For instance, it is possible to measure magnetization transfer (MT) effects, in which magnetization is transferred between protons of mobile water (commonly referred to as the "free pool") and protons associated with semi-solid macromolecules such as lipids and other complex molecules (commonly referred to as the "bound pool"). The protons of the bound pool have ultrashort T2 relaxation and therefore a significantly broader absorption lineshape compared to the mobile protons. Applying off-resonance saturation RF pulses during an MRI procedure allows protons of the bound pool to be selectively saturated while keeping the mobile protons unaffected. The saturation is transferred to the free-water pool due to dipolar interactions and chemical exchange, resulting in MT contrast.

MT ratio (MTR) is commonly used to characterize magnetization transfer. However, MTR is not an intrinsic tissue property because it is influenced by the pulse sequence parameters. Quantitative MT approaches have been developed to measure tissue-specific MT parameters based on a two-pool model having a free-water pool and a bound pool as described above. The model specifies parameters including T1 and T2 for each pool, magnetization exchange rates between the two pools, and the molar fraction of protons that are bound to macromolecules, also known as bound pool fraction (BPF) or macromolecular proton fraction (MPF). MPF is a tissue-specific parameter that is directly linked to the macromolecular density and composition and is independent of acquisition parameters.

In clinical applications, however, extracting MPF from MRI data is challenging, in part because of the need to quantify multiple MT parameters, which requires multiple MRI scans using different acquisition parameters and complicated post-processing. Acquisition time can be reduced by estimating only the most clinically relevant parameters, including MPF. Various techniques have been proposed. Some of these techniques use a single off-resonance RF saturation measurement, combined with assumptions that cross-relaxation is sufficiently fast and that a T1 map has already been acquired (e.g., using additional MRI scans). Another approach involves labeling the spins of the mobile protons rather than saturating off-resonance spins associated with the bound pool, using techniques such as stimulated echo amplitude modulation (STEAM) and fitting to a mono-exponential longitudinal relaxation model at steady state. This avoids the need to acquire a T1 map; however, stimulated echo techniques have intrinsically low signal-to-noise. Accordingly, faster and more accurate techniques for MPF quantification would be desirable.

SUMMARY

Certain embodiments of the present invention relate to systems and methods for fast and robust quantification of magnetization transfer (MT) using off-resonance spin-lock MRI.

The techniques can be insensitive to variations of the inherent relaxation rates R1 (1/T1) and R2 (1/T2) of the free-water pool and to variations of the chemical exchange pool. The techniques can also be robust in the presence of inhomogeneity in the B1 RF and/or B0 magnetic fields.

Some embodiments relate to methods for quantifying parameters of magnetization transfer using an MRI apparatus. Multiple image acquisition processes can be performed to produce a set of MRI images, where each image acquisition process (i) in the plurality of image acquisition process includes applying an off-resonance spin-lock pulse having an RF amplitude ($\omega_1^{(i)}$) and a frequency offset from resonance ($\Delta\omega^{(i)}$). Based on the set of MRI images, parameters of magnetization transfer can be computed. In particular, a parameter $R_{mpfsl}$ can be computed, where $R_{mpfsl}$ is defined as $R_{mpfsl}=R_{1\rho}^{(2)}-R_{1\rho}^{(2)}$, where $R_{1\rho}^{(1)}$ is a first relaxation rate in the rotating frame responsive to a spin-lock pulse having a first RF amplitude $\omega_1^{(1)}$ and a first frequency offset $\Delta\omega^{(1)}$; $R_{1\rho}^{(2)}$ is a second relaxation rate in the rotating frame responsive to a spin-lock pulse having a second RF amplitude $\omega_1^{(2)}$ and a second frequency offset $\Delta\omega^{(2)}$; and the first RF amplitude $\omega_1^{(1)}$, the first frequency offset $\Delta\omega^{(1)}$, the second RF amplitude $\omega_1^{(2)}$, and the second frequency offset $\Delta\omega^{(2)}$ are chosen such that $\Delta\omega^{(1)}/\omega_1^{(1)}=\Delta\omega^{(2)}/\omega_1^{(2)}$. Additional parameters of magnetization transfer can also be computed, such as: a macromolecular proton fraction (MPF)

indicating a fraction of protons that are bound to semi-solid macromolecules; a pool size ratio ($f_b$) for a magnetization transfer pool; an exchange rate ($k_{ba}$) between the magnetization transfer pool and a free-water pool; and/or a transverse relaxation time of the magnetization transfer pool ($T_{2b}$).

In various embodiments, different image-acquisition approaches may be used to determine $R_{mprsl}$. For example, in some embodiments, a set of four images can be acquired, two images at each of two combinations of spin-lock parameters. For each combination of spin-lock parameters one image is acquired with a toggling RF pulse applied before the spin-lock pulse and one image is acquired without a toggling RF pulse. From the four images, relaxation parameter $R_{mprsl}$ can be computed.

In other embodiments, a first image acquisition process uses a first spin-lock pulse at the first RF amplitude $\omega_1^{(1)}$ and the first frequency offset $\Delta\omega^{(1)}$ with a spin-lock time of zero to determine a first magnetization value; a second image acquisition process uses a second spin-lock pulse at the first RF amplitude $\omega_1^{(1)}$ and the first frequency offset $\Delta\omega^{(1)}$ with a spin-lock time greater than zero to determine a second magnetization value; and a third image acquisition process uses a third spin-lock pulse at the second RF amplitude $\omega_1^{(2)}$ and the second frequency offset $\Delta\omega^{(2)}$ to determine a third magnetization value. Where an observed longitudinal relaxation rate ($R_{1obs}$) and an equilibrium magnetization ($M_0$) are known (or where the product $R_{1obs} \cdot M_0$ is known), relaxation parameter $R_{mpfsl}$ can be computed by computing the first relaxation rate $R_{1\rho}^{(1)}$ based on the first magnetization value and the second magnetization value and computing the second relaxation rate $R_{1\rho}^{(2)}$ based on the first magnetization value and the Rip third magnetization value, then subtracting.

In other embodiments, the first subset of the image acquisition processes and the second subset of the image acquisition processes each include at least two image acquisition processes (so that the total number of image acquisition processes is at least four). Each image acquisition process in the first subset uses a spin-lock pulse having a time of spin-lock (TSL) that is different from the TSL of each other image acquisition process in the first subset, and each image acquisition process in the second subset uses a spin-lock pulse having a TSL that is different from the TSL of each other image acquisition process in the second subset. The first relaxation rate $R_{1\rho}^{(1)}$ and the second relaxation rate $R_{1\rho}^{(2)}$ can be computed from the plurality of images by finding optimized solutions to equations characterizing the magnetization as a function of TSL. In some embodiments, the pulse sequence can also be designed to provide a predictable relationship between the initial magnetization at the beginning of spin-lock and the equilibrium magnetization.

The following detailed description, together with the accompanying drawings, provides a further understanding of the nature and advantages of the claimed invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A shows an $R_{mpfsl}$ map as a function of frequency of spin-lock (FSL) and frequency offset (FO). FIG. 3B shows the corresponding relative percentage error between the exact $R_{mpfsl}$ and the approximate $R_{mpfsl}$. FIG. 3C shows the exact $R_{mpfsl}$ and the approximate $R_{mpfsl}$ as a function of FO under various conditions. FIG. 3D shows the exact $R_{mpfsl}$ and the approximate $R_{mpfsl}$ as a function of FSL under various conditions. FIG. 3E shows the exact $R_{mpfsl}$ and the approximate $R_{mpfsl}$ as a function of the scaling factor $N=\Delta\omega^{(2)}/\Delta\omega^{(1)}$.

DETAILED DESCRIPTION

Examples (also referred to as "embodiments") of systems and methods that provide quantification of parameters of magnetization transfers are described in this section. According to these and other embodiments, parameters of magnetization transfer can be quantified using spin-lock magnetic resonance imaging (MRI) techniques. It is noted that spin-lock also occurs during saturation RF pulses; accordingly, in embodiments described herein, off-resonance spin-lock RF pulse clusters or saturation RF pulses can be applied, and the term "spin-lock pulse" is used to refer to both spin-lock pulse clusters and saturation RF pulses. A series of acquisitions can be performed to provide a final measurement that is specific to the MT pool and independent of the free-water pool and the chemical exchange pool. As will become apparent, embodiments described herein allow quantification of magnetization transfer without acquisition of a T1 map or any assumption about the relaxation properties of the free-water pool.

MRI Systems

Figure 1:
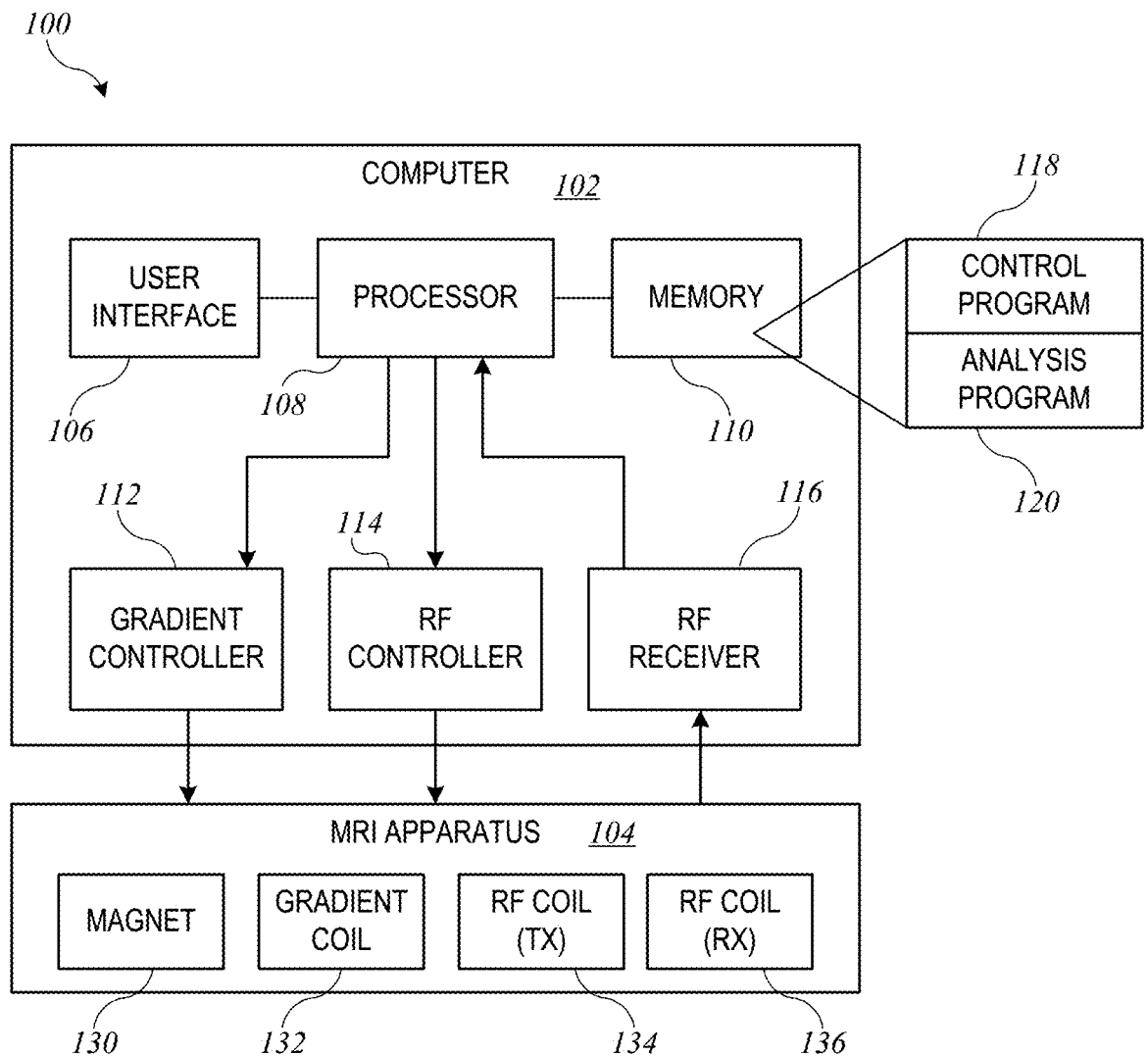
FIG. 1 shows an MRI system that can be used in connection with practicing some embodiments of the present invention.

FIG. 1 shows an MRI system that can be used in connection with practicing some embodiments of the present invention. MRI system 100 includes a computer 102 communicably coupled to an MRI apparatus 104.

Computer 102 can be of generally conventional design and can include a user interface 106, a processor 108, a memory 110, a gradient controller 112, an RF controller 114, and an RF receiver 116. User interface 106 can include components that allow a user (e.g., an operator of MRI system 100) to input instructions or data and to view information. For example, user interface 106 can include a keyboard, mouse, joystick, display screen, touch-sensitive display screen, and so on. Processor 108 can include a general purpose programmable processor (or any other processor or set of processors) capable of executing program code instructions to perform various operations. Memory 110 can include a combination of volatile and nonvolatile storage elements (e.g., DRAM, SRAM, flash memory, magnetic disk, optical disk, etc.). Portions of memory 110 can store program code to be executed by processor 108. Examples of the program code can include a control program 118, which can coordinate operations of MRI apparatus 104 as described below in order to acquire data, and an analysis program 120, which can perform analysis algorithms on data acquired from MRI apparatus 104 (e.g., as described below). Gradient controller 112, RF controller 114, and RF receiver 116 can incorporate standard communication interfaces and protocols to communicate with components of MRI apparatus 104 as described below.

MRI apparatus 104 can be of generally conventional design and can incorporate a magnet 130, a gradient coil 132, and RF coils 134, 136. Magnet 130 can be a magnet capable of generating a large constant magnetic field B0 (e.g., 1.5 T, 3.0 T, or the like) in a longitudinal direction, in a region where a patient (or other subject to be imaged) can be placed. Gradient coil 132 can be capable of generating gradients in the constant magnetic field B0; operation of gradient coil 132 can be controlled by computer 102 via gradient controller 112. RF coils 134, 136 can include a transmitter (TX) coil 134 and a receiver (RX) coil 136. In some embodiments, a single coil can serve as both transmitter and receiver. In some embodiments, RF transmitter coil 134 can be placed around the portion of the subject's body that is to be imaged while RF receiver coil 136 is placed elsewhere within MRI apparatus 104. The preferred placement of RF coils 134, 136 may depend on the specific portion of the body that is to be imaged; those skilled in the art with access to the present disclosure will be able to make appropriate selections.

In operation, computer 100 can drive gradient coil 132 using gradient controller 112 to shape the magnetic field around the region being imaged. Computer 100 can drive RF transmitter coil 134 using RF controller 114 to generate RF pulses at a desired frequency (e.g., a resonant frequency for an isotope of interest), driving nuclear spins into an excited state. RF receiver coil 136 can detect RF waves generated by the spins relaxing from the excited state when RF pulses are not being generated. RF receiver 116 can include amplifiers, digital-to-analog converters, and other circuitry to generate digital data from the RF waves detected by RF receiver coil 136. RF receiver 116 can provide this data to processor 108 for analysis.

MRI system 100 is illustrative, and many variations and modifications are possible. Those skilled in the art will be familiar with a variety of MRI apparatus and control systems and with basic principles of MRI data acquisition, including the use of gradient fields and RF pulses, as well as techniques for detecting signals responsive to RF pulses and processing those signals to generate images.

In some embodiments, MRI system 100 or other MRI apparatus can be used to generate pulse sequences suitable for MT imaging of a subject, such as a specific organ or tissue within a patient. Examples of pulse sequences and imaging operations are described below.

Typical MRI imaging processes include a "preparation" phase and an "acquisition" phase. During the preparation phase, various pulse sequences can be generated in RF transmitter coil 136 to create a desired state of the magnetization vectors of nuclei of interest. For instance, a "reset" sequence may be used to reset net magnetization such that net magnetization becomes zero. Other types of preparation can include pulse sequences designed to suppress signals from specific types of tissue not of interest (e.g., blood, fat). In embodiments described herein, the magnetization preparation sequence can include a spin-lock RF pulse cluster or a saturation RF pulse. A spin-lock RF pulse cluster consists of a tip-down RF pulse, a spin-lock RF pulse, and a tip-up RF pulse. A saturation RF pulse includes a spin-lock RF pulse without a tip-down RF pulse or tip-up RF pulse. Spin-lock can also occur during a saturation RF pulse, and the term "spin-lock pulse" is used herein to encompass a spin-lock RF pulse cluster or a saturation RF pulse (or other pulses or pulse clusters during which spin-lock occurs). The spin-lock RF pulse or saturation RF pulse is applied for a specified time duration (referred to as the time of spin-lock, or TSL). Some magnetization preparation sequences can also include a toggling RF pulse. After the preparation phase, acquisition can be performed using various sequences such as fast spin echo sequences or other sequences as desired.

MPF Quantification Process

Certain embodiments described herein perform MPF quantification. In some embodiments, a two-pool model is used, in which the measured relaxation rate is based on contributions from two different magnetization pools: a free-water pool (also referred to as "pool a") and a pool of protons bound to macromolecules (also referred to as a "bound pool" or "pool b"). The model assumes that magnetization exchanges can occur between the free-water and bound pools at some rate. The fractional sizes of the two pools are initially unknown. The notation shown in Table 1 is used to denote various parameters of the two pools.

TABLE 1

| | |
|---|---|
| $R_{1a} = 1/T_{1a}$ | Longitudinal relaxation rate of pool a (free-water pool) |
| $R_{1b} = 1/T_{1b}$ | Longitudinal relaxation rate of pool b (bound pool) |
| $R_{2a} = 1/T_{2a}$ | Transverse relaxation rate of pool a |
| $R_{2b} = 1/T_{2b}$ | Transverse relaxation rate of pool b |
| $f_a, f_b$ | Pool size ratios of pools a and b ($f_a = 1$) |
| $k_{ba}, k_{ab}$ | Exchange rates between pool b and pool a |

According to the two-pool model, for a spin-lock pulse having an RF amplitude $\omega_1$ and resonance frequency offset $\Delta\omega$), the relaxation rate during spin-lock ($R_{1\rho}$) can be derived by solving the Bloch-McConnell equation:

$$R_{1\rho}(\Delta\omega,\omega_1) = R_{water}(\Delta\omega,\omega_1) + R_{mt}(\Delta\omega,\omega_1) \qquad (1)$$

where $R_{water}$ is the effective relaxation rate of the water in the rotating frame and $R_{mt}$ is the MT-dependent relaxation rate. The effective relaxation rate $R_{water}$ can be expressed as:

$$R_{water} = R_{1a}\cos^2\theta + R_{2a}\sin^2\theta, \qquad (2)$$

where $$\sin^2\theta = \frac{\omega_1^2}{\omega_1^2 + \Delta\omega^2}, \cos^2\theta = \frac{\Delta\omega^2}{\omega_1^2 + \Delta\omega^2}. \qquad (3)$$

The MT-dependent relaxation rate $R_{mt}$ can be expressed as:

$$R_{mt} = \frac{(\Delta\omega^2 + r_{2a}^2)(k_{ba}r_{1a} + r_{1b}(k_{ab} + r_{1a})) + \omega_1^2 r_{2a}(k_{ba} + r_{1b})}{(\Delta\omega^2 + r_{2a}^2)(k_{ab} + k_{ba} + r_{1a} + r_{1b}) + 2r_{2a}(k_{ba}r_{1a} + r_{1b}(k_{ab} + r_{1a})) + \omega_1^2(r_{2a} + k_{ba} + r_{1b})}, \quad (4)$$

where $r_{1a} = R_{1a} - R_{water}$; $r_{2a} = R_{2a} - R_{water}$; and $r_{1b} = R_{1b} + R_{rfc} - R_{water}$, where $R_{rfc}$ represents the saturation rate of the bound pool. The saturation rate of the bound pool $R_{rfc}$ is a function of the RF amplitude ($\omega_1$), off-resonance frequency ($\Delta\omega$), and $T_{2b}$. In some embodiments, $R_{rfc}(\Delta\omega) = \omega_1^2 \pi g_b(\Delta\omega)$, where $$g_b(\Delta\omega) = T_{2b} \int_0^1 \frac{1}{|3u^2 - 1|} \sqrt{\frac{2}{\pi}} \exp\left(-2\left(\frac{\Delta\omega \cdot T_{2b}}{3u^2 - 1}\right)^2\right) du \quad (5)$$

is the super-Lorentzian lineshape for the bound pool. Other lineshapes, such as Gaussian lineshape, can also be used in some embodiments. A derivation of Eq. (4) as an analytical expression of MT-dependent relaxation based on the eigenspace solution of the Bloch-McConnell equation has been shown in Zaiss et al., "A combined analytical solution for chemical exchange saturation transfer and semi-solid magnetization transfer," NMR in Biomedicine 28(2):217-30 (2015).

Macromolecular proton fraction (MPF) can be defined as:

$$MPF = \frac{f_b}{1 + f_b}. \quad (6)$$

According to some embodiments, MPF can be quantified by measuring the difference of $R_{1\rho}$ from two determinations at two different combinations of off-resonance frequency and RF amplitude of the spin-lock pulse. (It should be understood that for off-resonance spin-lock, $\Delta\omega \neq 0$.) This parameter is defined as $R_{mpfsl}$. Specifically:

$$R_{mpfsl} = R_{1\rho}^{(2)} - R_{1\rho}^{(1)} = R_{1\rho}(\Delta\omega^{(2)}, \omega_1^{(2)}) - R_{1\rho}(\Delta\omega^{(1)}, \omega_1^{(1)}) = \Delta R_{water} + \Delta R_{mt}, \quad (7)$$

where superscripts $^{(1)}$ and $^{(2)}$ denote the different acquisitions. If the off-resonance frequencies and RF amplitudes for the two acquisitions satisfy the following condition:

$$\Delta\omega^{(1)}/\omega_1^{(1)} = \Delta\omega^{(2)}/\omega_1^{(2)}, \quad (8)$$

then Eq. (3) gives $\theta^{(1)} = \theta^{(2)}$, and Eq. (2) yields $\Delta R_{water} = 0$.

In some embodiments, the off-resonance frequencies $\Delta\omega^{(1)}$ and $\Delta\omega^{(2)}$ are chosen such that:

$$\Delta\omega^{(1)}/\omega_1^{(1)} \gg 1 \quad (9)$$

and $$\Delta\omega^{(1)} \gg R_{2a}. \quad (10)$$

For living tissue, $R_{2a}$ is on the order of tens of Hertz. Under the conditions of Eqs. (9) and (10), $r_{1a} \approx 0$ and $r_{1c} \approx R_{rfc}$. Thus, applying Eq. (4), Eq. (7) becomes:

$$R_{mpfsl} = \quad (11)$$
$$\Delta R_{mt} = k_{ba}^2 f_b (1 + f_b) \left( \frac{1}{(1 + f_b)k_{ba} + R_{rfc}^{(1)}} - \frac{1}{(1 + f_b)k_{ba} + R_{rfc}^{(2)}} \right).$$

Figure 2:
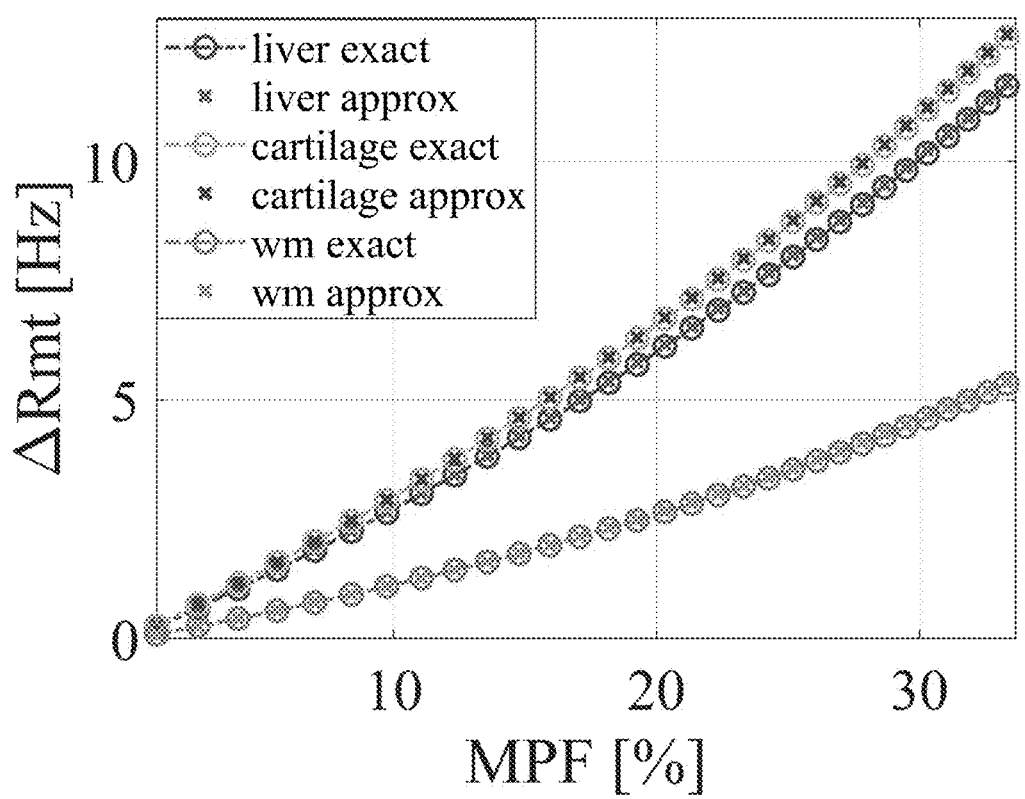
FIG. 2 is a graph showing results of approximate and exact computations of a relaxation parameter $R_{mpfsl}$ for various tissue types and macromolecular proton fraction (MPF) according to some embodiments.

FIG. 2 is a graph showing results of Eq. (11) ("approx") compared to an "exact" $R_{mprsl}$ computed using Eqs. (4), (7), and (8) without approximations, for three different tissue types: liver, cartilage, and white matter (wm) at different values of MPF. For purposes of the computations, MT parameters from previously published work were used. Parameter values for liver, cartilage, and white matter, respectively, were: $T_{1a} = T_{1b} = 812$ ms, 1168 ms, and 1084 ms; $T_{2a} = 42$ ms, 27 ms, and 69 ms; $T_{2b} = 7.7$ μs, 8.3 μs, and 10 μs; $f_b = 6.9\%$, 17.1%, and 13.9%; $k_{ba} = 51$ s$^{-1}$, 57 s$^{-1}$, and 23 s$^{-1}$. In all cases, the off-resonance spin-lock parameters for the two acquisitions were: $\Delta\omega^{(1)} = 2\pi \cdot 1000$ Hz, $\Delta\omega^{(2)} = 2\pi \cdot 4000$ Hz, $\omega_1^{(1)} = 2\pi \cdot 100$ Hz, and $\omega_1^{(2)} = 2\pi \cdot 400$ Hz. In all cases, Eq. (11) provides a very close approximation to an exact computation of $R_{mpfsl}$ across the range of MPF values. As shown in FIG. 2, $R_{mpfsl}$ increases monotonically with MPF, which is a function of $f_b$ according to Eq. (6).

According to various embodiments, Eq. (11) forms the basis of an approach to MPF quantification. From Eqs. (6) and (11), it follows that MPF can be computed from a measurement of $R_{mprsl}$ if the values of $k_{ba}$ and $T_{2b}$ are known. With regard to $k_{ba}$ and $T_{2b}$, it has been shown that, for some applications, these parameters vary only within a narrow range from subject to subject. Accordingly, in some embodiments it can be assumed that $k_{ba}$ and $T_{2b}$ are constant, and published values can be used. Alternatively, $k_{ba}$ and $T_{2b}$ can be treated as variables, and MPF can be computed by fitting data from multiple acquisitions to Eq. (11). It is noted that a T1 map is not needed in order to extract MPF from measured $R_{mpfsl}$. Computing MPF from $R_{mpfsl}$ may require a B1 map; however, a B1 map can be obtained quickly using conventional methods (or other methods that may be subsequently developed).

As noted above, the derivation of Eq. (11) assumes that the condition of Eq. (8) holds. Eq. (8) holds if $\Delta\omega^{(2)} = N\Delta\omega^{(1)}$ and $\omega_1^{(2)} = N\omega_1^{(1)}$ for a constant scaling factor N (which can be, but need not be, an integer). Thus, the RF amplitudes $\omega_1^{(1)}$, $\omega_1^{(2)}$ and resonance frequency offsets $\Delta\omega^{(1)}$, $\Delta\omega^{(2)}$ can be determined by selecting $\omega_1^{(1)}$, $\Delta\omega^{(1)}$, and N. The particular values are a matter of design choice, which can be guided by the following considerations. First, the frequency offset for each acquisition should be large enough to satisfy Eqs. (9) and (10). Second, the derivation of Eq. (11) ignores the presence of a chemical exchange pool, which can contribute to $R_{1\rho}$ and thus confound the measurement of $R_{mprsl}$. To avoid the confounding effect of chemical exchange, $\Delta\omega$ can be chosen to be far away from the chemical shift of the chemical exchange pool. Third, the choice of $\omega_1^{(1)}$, $\Delta\omega^{(1)}$, and N affects the signal level of $R_{mpfsl}$.

Figures 3A, 3B, 3C, 3D, 3E:
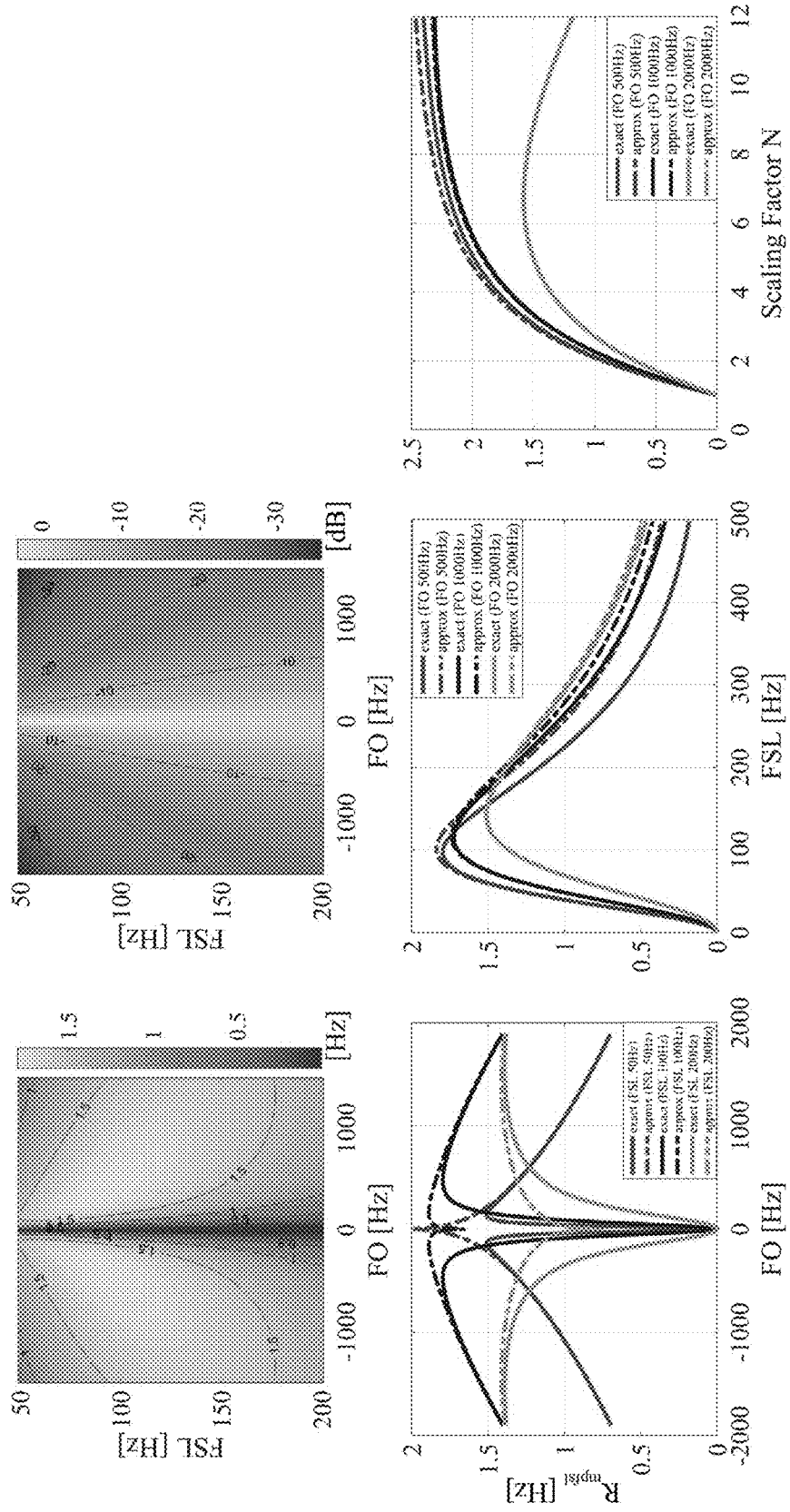
FIGS. 3A-3E show an example of the relationship between relaxation parameter $R_{mpfsl}$ and RF amplitude of the spin-lock RF pulse (or saturation RF pulse), $\omega_1^{(1)}$, also referred to as frequency of spin-lock (FSL), frequency offset $\Delta\omega^{(1)}$, and scaling factor $N=\Delta\omega^{(2)}/\Delta\omega^{(1)}$, using parameters for liver, as computed using full-equation Bloch-McConnell simulations according to some embodiments.

The particular relationship between $R_{mpfsl}$ and a particular choice of coin, $\omega_1^{(1)}$, $\omega_1^{(2)}$, $\Delta\omega^{(1)}$, $\Delta\omega^{(2)}$ can be modeled using full-equation Bloch-McConnell simulations. FIGS. 3A-3E show an example of the relationship between $R_{mpfsl}$ and spin-lock frequency $\omega_1^{(1)}$ (denoted as FSL in FIGS. 3A-3D) and frequency offset $\Delta\omega^{(1)}$ (denoted as FO in FIGS. 3A-3E) according to some embodiments, using parameters for liver, as computed using full-equation Bloch-McConnell simulations. FIG. 3A shows an $R_{mpfsl}$ map as a function of FSL and FO, for N=4. FIG. 3B shows the corresponding relative percentage error in decibels (dB) between the exact $R_{mpfsl}$ and the approximate $R_{mpfsl}$. FIG. 3C shows the exact $R_{mpfsl}$ and the approximate $R_{mpfsl}$ as a function of FO for N=4 and FSL=50 Hz, 100 Hz, and 200 Hz, respectively. FIG. 3D shows the exact $R_{mpfsl}$ and the approximate $R_{mpfsl}$ as a function of FSL for N=4 and FO=500 Hz, 1000 Hz, and 2000 Hz, respectively. FIG. 3E shows the exact $R_{mpfsl}$ and the approximate $R_{mpfsl}$ as a function of scaling factor N for FSL=100 Hz and FO=500 Hz, 1000 Hz, and 2000 Hz, respectively.

Based on FIGS. 3A-3E, choice of the frequency offset $\Delta\omega^{(1)}$ (or FO) can be guided by observing that the error due to approximation rises when frequency offset is small, due to violation of Eqs. (9) and (10), as best seen in FIG. 3C. Accordingly, increased frequency offset helps to maintain accuracy of Eq. (11) when spin-lock frequency $\omega_1^{(1)}$ (or FSL) increases; however higher frequency offset may lead to signal loss, as shown in FIG. 3B. Further, for a given frequency offset, an optimal spin-lock frequency can be defined as the spin-lock frequency that maximizes $R_{mpfsl}$ at the given frequency offset (as shown in FIG. 3D). In clinical practice, the choice of spin-lock frequency FSL may also be constrained by the specific absorption rate (SAR) limit, as larger values may lead to disfavored high SAR deposition. Similarly, the choice of N can be guided by the observation that small N is preferred from an SAR perspective, while the $R_{mpfsl}$ signal becomes small for small N (as shown in FIG. 3E). While liver tissue is used in this example, simulation studies of other tissue lead to similar considerations.

In some embodiments, these considerations lead to the following choice of parameter values: $\Delta\omega^{(1)}=2\pi\cdot1000$ Hz $\omega_1^{(1)}=2\pi\cdot100$ Hz, and N=4. These parameter values are used in examples below; however, it should be understood that different parameter values may be chosen.

Acquisition Processes for $R_{mpfsl}$

As described above, MPF and other magnetization transfer parameters can be determined from one or more measurements of $R_{mpfsl}$, which is defined as the difference of $R_{1\rho}$ from two data acquisitions at two different combinations of off-resonance frequency and RF amplitude of the spin-lock pulse. In some embodiments, $R_{1\rho}$ can be measured using off-resonance spin-lock techniques in which a spin-lock RF pulse cluster is applied, followed by imaging data acquisition. A spin-lock RF pulse cluster can include a tip-down RF pulse, a spin-lock RF pulse, and a tip-up RF pulse. The tip-down RF pulse flips the longitudinal magnetization at a specific flip angle determined by the selected spin-lock frequency $\omega_1$ and frequency offset $\Delta\omega$. After the tip-down pulse, the spin-lock RF pulse is applied for a duration in parallel with the magnetization and locks the spin at the specific flip angle. After the spin-lock RF pulse, the tip-up RF pulse flips the spin back to the longitudinal direction. Either hard pulses or adiabatic pulses can be used for the tip-down and tip-up RF pulses. In some embodiments, a saturation RF pulse can be used instead of a spin-lock RF pulse cluster. For saturation RF pulses, there is only a saturation (or spin-lock) RF pulse, with no tip-down or tip-up RF pulse. Where a saturation RF pulse is used, the time duration of the pulse may be much longer than the duration of the spin-lock RF pulse of a spin-lock RF pulse cluster, and the B1 amplitude of the saturation RF pulse may be much smaller than the B1 amplitude of the spin-lock RF pulse of a spin-lock RF pulse cluster. The term "spin-lock pulse" is used herein to encompass a spin-lock RF pulse cluster or a saturation RF pulse (or other pulses or pulse clusters during which spin-lock occurs).

Four approaches to measuring $R_{mpfsl}$ will now be described. It should be understood that these approaches are illustrative and not limiting.

According to a first approach, $R_{mpfsl}$ is obtained by a direct measurement, without separately measuring $R_{1\rho}^{(1)}$ and $R_{1\rho}^{(2)}$. Direct measurement of $R_{mpfsl}$ can involve combining a toggling RF pulse with an off-resonance spin-lock pulse (including a spin-lock RF pulse cluster or saturation RF pulse) to obtain magnetization-prepared images. Toggling RF pulses are described, e.g., in Alex K. Smith et al., "Rapid, High-Resolution Quantitative Magnetization Transfer Mill of the Human Spinal Cord," *NeuroImage* 95:106-16, https://doi.org/10.1016/j.neuroimage.2014.03.005 (Jul. 15, 2014), and Tao Jin and Seong-Gi Kim, "Quantitative Chemical Exchange Sensitive Mill Using Irradiation with Toggling Inversion Preparation," *Magnetic Resonance in Medicine* 68(4):1056-64, https://doi.org/10.1002/mrm.24449 (2012). The toggling RF pulse can be applied (or not) prior to the spin-lock pulse.

For example, four images can be acquired. Specifically, under each of two different conditions of spin-lock $(\Delta\omega^{(1)}, \omega_1^{(1)})$ and $(\Delta\omega^{(2)}, \omega_1^{(1)})$ selected as described above, two images are obtained: a first image is obtained with the toggling RF pulse turned on ($M_{Tog}^{(1)}$ and $M_{Tog}^{(2)}$), and a second image is obtained with the toggling RF pulse turned off ($M_{noTog}^{(1)}$ and $M_{noTog}^{(2)}$). If the same duration of the spin-lock RF pulse or the saturation RF pulse (denoted as TSL) is used for all four acquisitions, then $R_{mpfsl}$ can be computed as:

$$R_{mpfsl} = R_{1\rho}^{(2)} - R_{1\rho}^{(1)} = -\log\left(\frac{M_{Tog}^{(2)} - M_{noTog}^{(2)}}{M_{Tog}^{(1)} - M_{noTog}^{(1)}}\right)/TSL. \quad (12)$$

Figure 4:
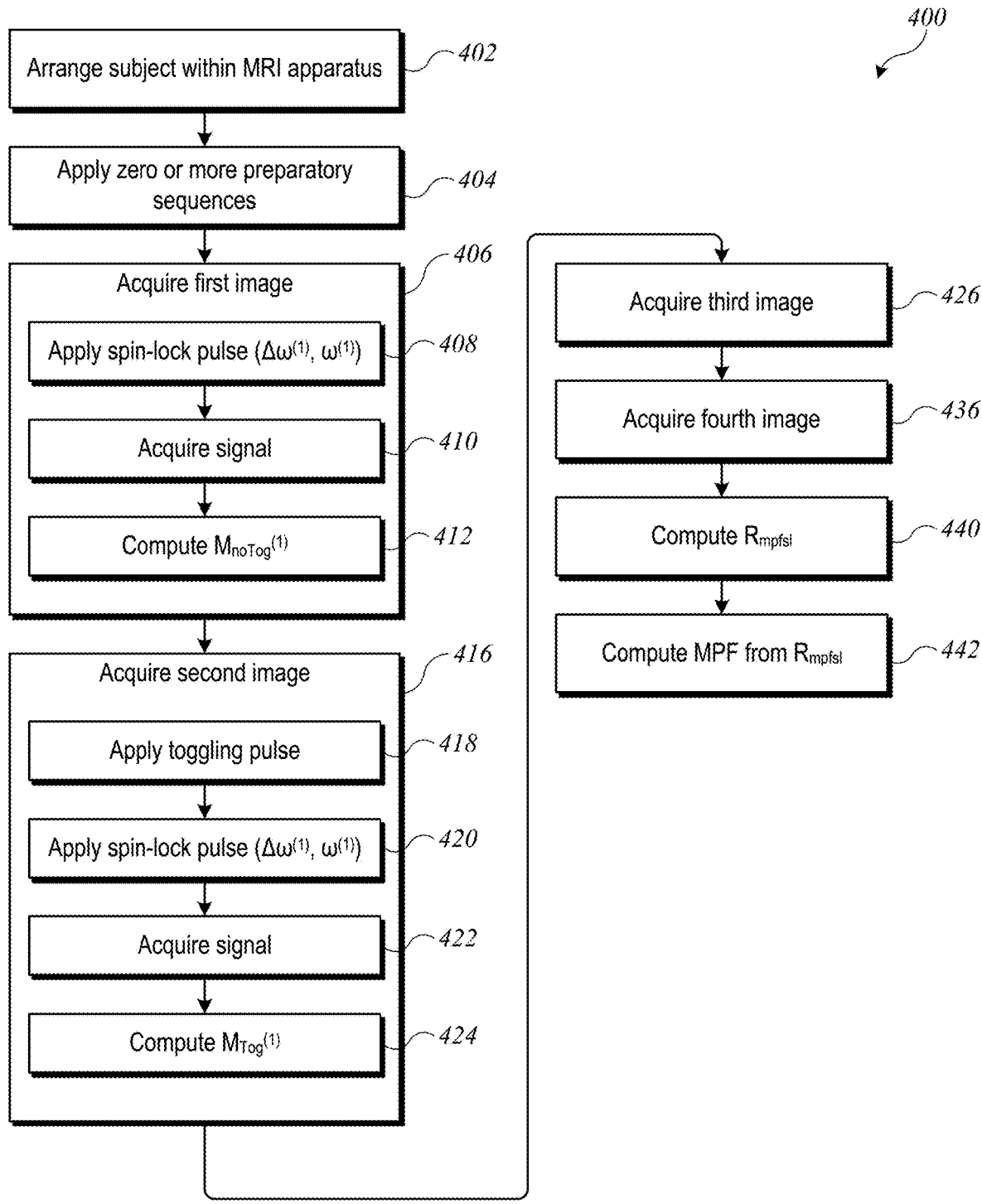
FIG. 4 shows a flow diagram of a first process for determining MPF according to some embodiments.

FIG. 4 shows a flow diagram of a process 400 for determining MPF according to some embodiments. Process 400 can be performed using an MRI apparatus such as MRI apparatus 100 of FIG. 1. At block 402, a subject (e.g., a patient whose tissue is to be imaged) is arranged within an MRI apparatus. This can include having the patient assume a supine or other desired position and aligning the patient within the MRI apparatus. In some embodiments, this may also include positioning of RF and/or gradient coils; the particular positioning will depend on what is being imaged.

At block 404, various preparatory pulse sequences can be applied. Examples include magnetization reset sequences, sequences to reduce the effect of selected tissue types (e.g., blood, fat, etc.), and the like. Such sequences can be conventional and are optional; a detailed description is omitted as not being critical to understanding the claimed invention.

At block 406, a first image acquisition is performed. In some embodiments, the first image acquisition can include applying a spin-lock pulse (including a spin-lock RF pulse cluster or a saturation RF pulse) with characteristics $(\Delta\omega^{(1)}, \omega_1^{(1)})$ at block 408, followed by signal acquisition at block 410. Signal acquisition can include generating RF pulses to stimulate a signal from the subject and operating an RF receiver coil to detect the signal. Various acquisition sequences can be performed, including single-shot or multi-shot fast spin echo (FSE) sequences; other acquisition sequences and techniques suitable for quantifying R1ρ can also be used. During the signal acquisition, a first data set can be collected. At block 412, a first image $M_{noTog}^{(1)}$ can be computed based on the data set. Conventional techniques for generating images from acquired MRI data can be used; examples include Fourier transform of acquired k-space data.

At block 416, a second image acquisition is performed. In some embodiments, the second image acquisition can include applying a toggling RF pulse at block 418, followed by applying a spin-lock RF pulse (including a spin-lock RF pulse cluster or a saturation RF pulse) with characteristics $(\Delta\omega^{(1)}, \omega_1^{(1)})$ at block 420, followed by signal acquisition at block 422 to collect a second data set. Signal acquisition operations can be similar or identical to the signal acquisition operations at block 412. At block 424, a second image $M_{Tog}^{(1)}$ can be computed based on the data set collected at block 422, similarly to computation of the first image at block 412.

At block 426, a third image acquisition is performed. The third image acquisition can be similar to the first image acquisition at block 406, except that the spin-lock pulse has different characteristics $(\Delta\omega^{(2)}, \omega_1^{(1)})$, and the third image can be identified as $M_{noTog}^{(2)}$.

At block 436, a fourth image acquisition is performed. The fourth image acquisition can be similar to the second image acquisition at block 416, except that the spin-lock pulse has different characteristics $(\Delta\omega^{(2)}, \omega_1^{(1)})$ and the fourth image can be identified as $M_{Tog}^{(2)}$.

At block 440, relaxation parameter $R_{mpfsl}$ can be computed from the four images, e.g., according to Eq. (12). At block 442, MPF can be computed from $R_{mpfsl}$, e.g., according to Eqs. (11) and (6).

Process 400 is illustrative, and variations or modifications are possible. For instance, acquisition of the images can occur in any order. In this example, all four acquisitions use the same (nonzero) TSL, and TSL can be chosen as desired. Off-resonance frequencies and RF amplitudes for the spin-lock pulses (which can include a spin-lock RF pulse cluster or a saturation RF pulse) can be chosen as desired, subject to Eqs. (8)–(10). In some embodiments, crusher gradients can be applied after each spin-lock pulse and prior to each signal acquisition sequence. Fat suppression and/or other preparatory pulse sequences can be applied before or after each spin-lock pulse and prior to each signal acquisition sequence. Using process 400 or similar processes, $R_{mpfsl}$ can be determined directly from measured magnetizations (or images), without separately measuring $R_{1\rho}^{(1)}$ and $R_{1\rho}^{(2)}$.

According to a second approach, $R_{mpfsl}$ can be determined by obtaining $R_{1\rho}^{(1)}$ and $R_{1\rho}^{(2)}$ individually, then computing the difference. In the second approach, it can be assumed that the observed longitudinal relaxation rate ($R_{1obs}=1/T_{1obs}$, where $T_{1obs}$ is the observed T1 relaxation time) and equilibrium magnetization $M_0$ are known, or that the product $R_{1obs}\cdot M_0$ is known. $R_{1obs}$ and $M_0$ (or the product $R_{1obs}\cdot M_0$) can be determined using conventional approaches (or other approaches subsequently developed), and a detailed description is omitted. Where $R_{1obs}$ and $M_0$ are known or the product $R_{1obs}\cdot M_0$ is known, $R_{1\rho}^{(1)}$ and $R_{1\rho}^{(2)}$ can be quantified using three acquisitions.

For instance, the first acquisition can use the following parameters: TSL=0 ms, $\Delta\omega^{(1)}=2\pi\cdot 1000$ Hz, and $\omega_1^{(1)}=2\pi\cdot 100$ Hz. (It should be understood that when TSL=0 ms, $\Delta\omega^{(1)}$ and $\omega_1^{(1)}$ determine the flip angle of the tip-down and tip-up RF pulses, and there is no spin-lock RF pulse.) The measured magnetization for the first acquisition ($M^1$) can be expressed as:

$$M^1 = M_{ini}, \tag{13}$$

where $M_{ini}$ is the initial magnetization after the tip-down RF pulse and at the beginning of the spin-lock RF pulse or saturation RF pulse.

For the second acquisition, the parameters can be: TSL=50 ms (or other non-zero time), $\omega_1^{(1)}=2\pi\cdot 100$ Hz, and $\Delta\omega^{(1)}=2\pi\cdot 1000$ Hz. The measured magnetization at the end of spin-lock for the second acquisition ($M^2$) can be expressed as:

$$M^2 = M_{ini}\cdot e^{-R_{1\rho}^{(1)}\cdot TSL} + M_{SS1}\cdot\left(1-e^{-R_{1\rho}^{(1)}\cdot TSL}\right), \tag{14}$$

where $M_{ss1}$ is the steady-state magnetization. $M_{ss1}$ can be expressed as:

$$M_{ss1} = \frac{\cos\theta\cdot R_{1obs}}{R_{1\rho}^{(1)}}M_0, \tag{15}$$

where $\theta=\tan^{-1}(\omega_1^{(1)}/\Delta\omega^{(1)})$. Assuming $R_{1obs}$ and $M_0$ are known (or the product $R_{1obs}\cdot M_0$ is known), it follows that after substituting Eqs. (13) and (15) into Eq. (14), $R_{1\rho}^{(1)}$, is the only unknown variable. Accordingly, $R_{1\rho}^{(1)}$ can be computed by solving Eq. (14).

For the third acquisition, the parameters can be: $\omega_1^{(2)}=N\omega_1^{(1)}$ and $\Delta\omega^{(2)}=N\Delta\omega^{(1)}$, where N is a constant scaling factor. TSL can be the same as for the second acquisition or any other value greater than zero. The measured magnetization at the end of spin-lock for the third acquisition ($M^3$) can be expressed as:

$$M^3 = M_{ini}\cdot e^{-R_{1\rho}^{(2)}\cdot TSL} + M_{ss2}\cdot\left(1-e^{-R_{1\rho}^{(2)}\cdot TSL}\right), \tag{16}$$

where $M_{ss2}$ is the steady-state magnetization. $M_{ss2}$ can be expressed as:

$$M_{ss2} = \frac{\cos\theta\cdot R_{1obs}}{R_{1\rho}^{(2)}}M_0. \tag{17}$$

The same $M_{ini}$ from Eq. (13) can be used if the same spin-lock preparation type (i.e., hard RF pulse or adiabatic) was used in the first and third acquisitions. Similarly to the second acquisition, after substituting Eqs. (13) and (17) into Eq. (16), $R_{1\rho}^{(2)}$ is the only unknown variable. Accordingly, $R_{1\rho}^{(2)}$ can be computed by solving Eq. (16).

Once $R_{1\rho}^{(1)}$ and $R_{1\rho}^{(2)}$ have been computed, $R_{mpfsl}$ can be computed as $R_{mpfsl}=R_{1\rho}^{(2)}-R_{1\rho}^{(1)}$ according to Eq. (7).

Figure 5:
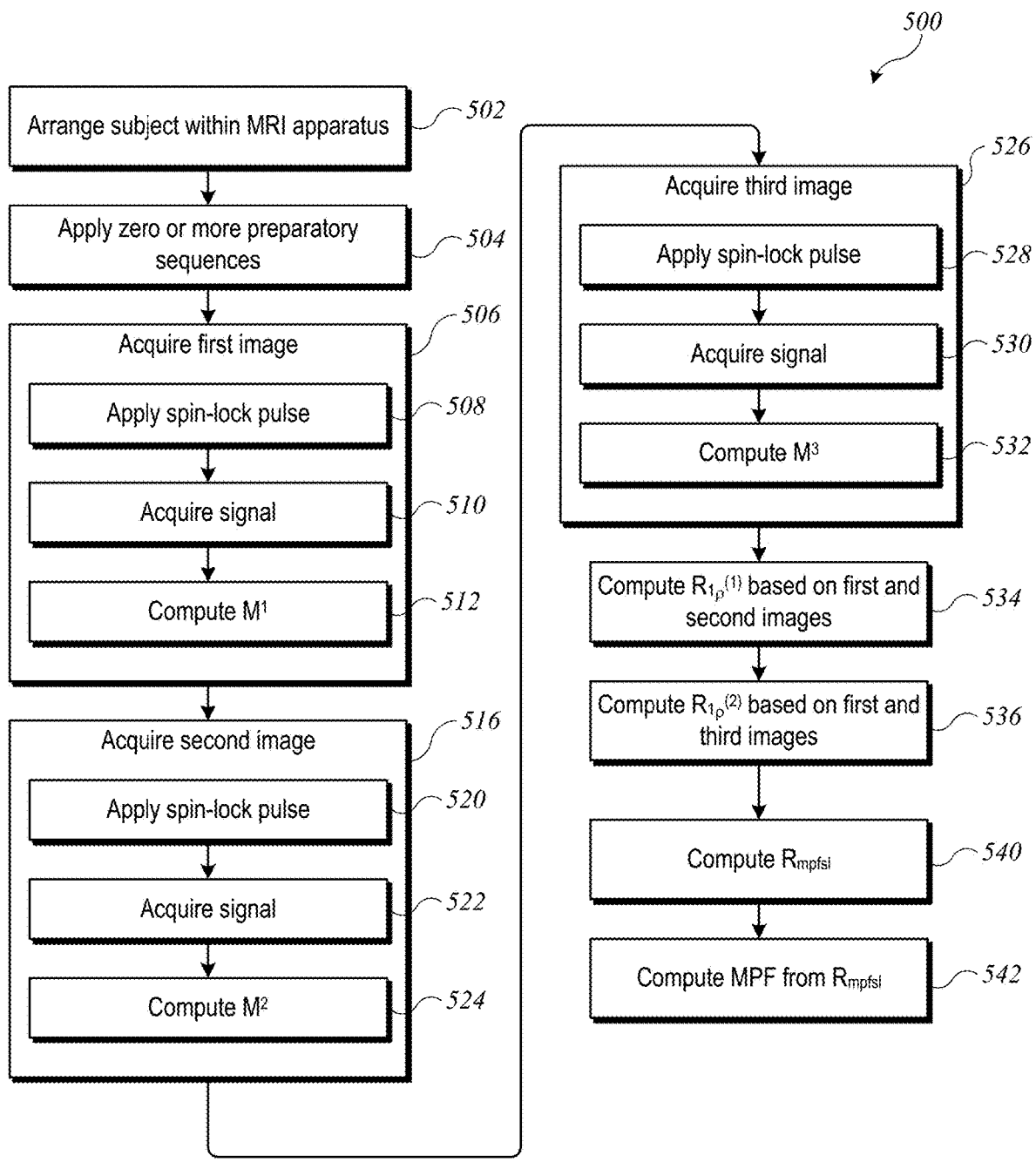
FIG. 5 shows a flow diagram of a second process for determining MPF according to some embodiments.

FIG. 5 shows a flow diagram of a process 500 for determining MPF according to some embodiments. Process 500 can be performed using an MRI apparatus such as MRI apparatus 100 of FIG. 1. At block 502, a subject (e.g., a patient whose tissue is to be imaged) is arranged within an MRI apparatus. This can include having the patient assume a supine or other desired position and aligning the patient within the MRI apparatus. In some embodiments, this may also include positioning of RF and/or gradient coils; the particular positioning will depend on what is being imaged.

At block 504, various preparatory pulse sequences can be applied. Examples include magnetization reset sequences, sequences to reduce the effect of selected tissue types (e.g., blood, fat, etc.), and the like. Such sequences can be conventional and are optional; a detailed description is omitted as not being critical to understanding the claimed invention.

At block 506, a first image acquisition is performed. In some embodiments, the first image acquisition can include applying a spin-lock pulse at block 508, with TSL=0 ms, $\Delta\omega^{(1)}=2\pi\cdot1000$ Hz, and $\omega_1^{(1)}=2\pi\cdot100$ Hz, followed by signal acquisition at block 510. Similarly to process 400, signal acquisition can include generating RF pulses to stimulate a signal from the subject and operating an RF receiver coil to detect the signal. Various acquisition sequences can be performed, including single-shot or multi-shot fast spin echo (FSE) sequences; other acquisition sequences and techniques suitable for quantifying R1ρ can also be used. During the signal acquisition, a first data set can be collected. At block 512, a first image $M^1$ can be computed based on the data set. Conventional techniques for generating images from acquired MRI data can be used; examples include Fourier transform of acquired k-space data.

At block 516, a second image acquisition is performed. In some embodiments, the second image acquisition can include applying a spin-lock pulse (including a spin-lock RF pulse cluster or a saturation RF pulse) at block 520, with TSL=50 ms (or other non-zero time), $\omega_1^{(1)}=2\pi\cdot100$ Hz, and $\Delta\omega^{(1)}=2\pi\cdot1000$ Hz, followed by signal acquisition at block 522 to collect a second data set. Signal acquisition operations can be similar or identical to the signal acquisition operations at block 510. At block 524, a second image $M^2$ can be computed based on the data set collected at block 522, similarly to computation of the first image at block 512.

At block 526, a third image acquisition is performed. In some embodiments, the third image acquisition can include applying a spin-lock pulse (including a spin-lock RF pulse cluster or a saturation RF pulse) at block 528 with TSL greater than zero, $\omega_1^{(2)}=N\omega_1^{(1)}$, and $\Delta\omega^{(2)}=N\Delta\omega^{(1)}$, where N is a constant scaling factor, followed by signal acquisition at block 530 to collect a third data set. Signal acquisition operations can be similar or identical to the signal acquisition operations at block 510. At block 532, a third image $M^3$ can be computed based on the data set collected at block 522, similarly to computation of the first image at block 512.

At block 534, $R_{1\rho}^{(1)}$ can be computed based on the first and second images, e.g., by solving Eq. (14) as described above. At block 536, $R_{1\rho}^{(2)}$ can be computed based on the first and third images, e.g., by solving Eq. (16) as described above. At block 540 relaxation parameter $R_{mpfsl}$ can be computed as $R_{mpfsl}=R_{1\rho}^{(2)}-R_{1\rho}^{(1)}$. At block 542, MPF can be computed from $R_{mpfsl}$, e.g., according to Eqs. (11) and (6).

Process 500 is illustrative, and variations or modifications are possible. For instance, acquisition of the images can occur in any order. Off-resonance frequencies and RF amplitudes for the spin-lock pulses (which can include a spin-lock RF pulse cluster or a saturation RF pulse) can be chosen as desired, subject to Eqs. (8)-(10). In some embodiments, crusher gradients can be applied after each spin-lock RF pulse cluster or saturation RF pulse and prior to each signal acquisition sequence. Fat suppression and/or other preparatory pulse sequences can be applied before or after each spin-lock RF pulse cluster or saturation RF pulse and prior to each signal acquisition sequence. Process 500 uses three acquisitions rather than four but assumes that $R_{1obs}$ and $M_0$ are known (or that the product $R_{1obs} M_0$ is known), which may require one or more additional acquisitions.

According to a third approach, $R_{mpfsl}$ can be determined by obtaining $R_{1\rho}^{(1)}$ and $R_{1\rho}^{(2)}$ individually, then computing the difference, but without knowledge of $R_{1obs}$ and $M_0$. For example, according to Eqs. (14) and (15), for an image acquisition i using RF amplitude $\omega_1^{(1)}$ and frequency offset $\Delta\omega^{(1)}$, magnetization after spin-lock $(M_i^{(1)})$ can be expressed as:

$$M_i^{(1)} = M_{ini} \cdot e^{-R_{1\rho}^{(1)} \cdot TSL_i^{(1)}} + \frac{\cos\theta \cdot R_{1obs}}{R_{1\rho}^{(1)}} \cdot M_0 \cdot \left(1 - e^{-R_{1\rho}^{(1)} \cdot TSL_i^{(1)}}\right), \quad (14')$$

where $TSL_i^{(1)}$ is the time of spin-lock for the ith acquisition. Similarly, according to Eqs. (16) and (17), for an image acquisition i using RF amplitude $\omega_1^{(2)}$ and frequency offset $\Delta\omega^{(2)}$, magnetization after spin-lock $(M_i^{(2)})$ can be expressed as:

$$M_i^{(2)} = M_{ini} \cdot e^{-R_{1\rho}^{(2)} \cdot TSL_i^{(2)}} + \frac{\cos\theta \cdot R_{1obs}}{R_{1\rho}^{(2)}} \cdot M_0 \cdot \left(1 - e^{-R_{1\rho}^{(2)} \cdot TSL_i^{(2)}}\right), \quad (16')$$

where $TSL_i^{(2)}$ is the time of spin-lock for the ith acquisition. In Eqs. (14') and (16'), $\theta=\tan^{-1}(\omega_1^{(1)}/\Delta\omega^{(1)})$ is known. $TSL_i^{(1)}$ or $TSL_i^{(2)}$ is also chosen for each acquisition and therefore known, and $M_i^{(1)}$ or $M_i^{(2)}$ is determined from acquired signal. Accordingly, Eqs. (14') and (16') involve four unknowns: $M_{ini}$, $R_{1\rho}^{(1)}$, $R_{1\rho}^{(2)}$, and the product $M_0 \cdot R_{1obs}$. If at least two acquisitions i are performed using RF amplitude $\omega_1^{(1)}$ and frequency offset $\Delta\omega^{(1)}$ and at least two other acquisitions i are performed using RF amplitude $\omega_1^{(2)}$ and frequency offset $\Delta\omega^{(2)}$, with varying values of TSL, $R_{1\rho}^{(1)}$ and $R_{1\rho}^{(2)}$ can be derived from Eqs. (14') and (16') using traditional optimization approaches, neural networks, or other optimization procedures. $R_{mpfsl}$ can be computed as $R_{mpfsl}=R_{1\rho}^{(2)}-R_{1\rho}^{(1)}$.

Figure 6:
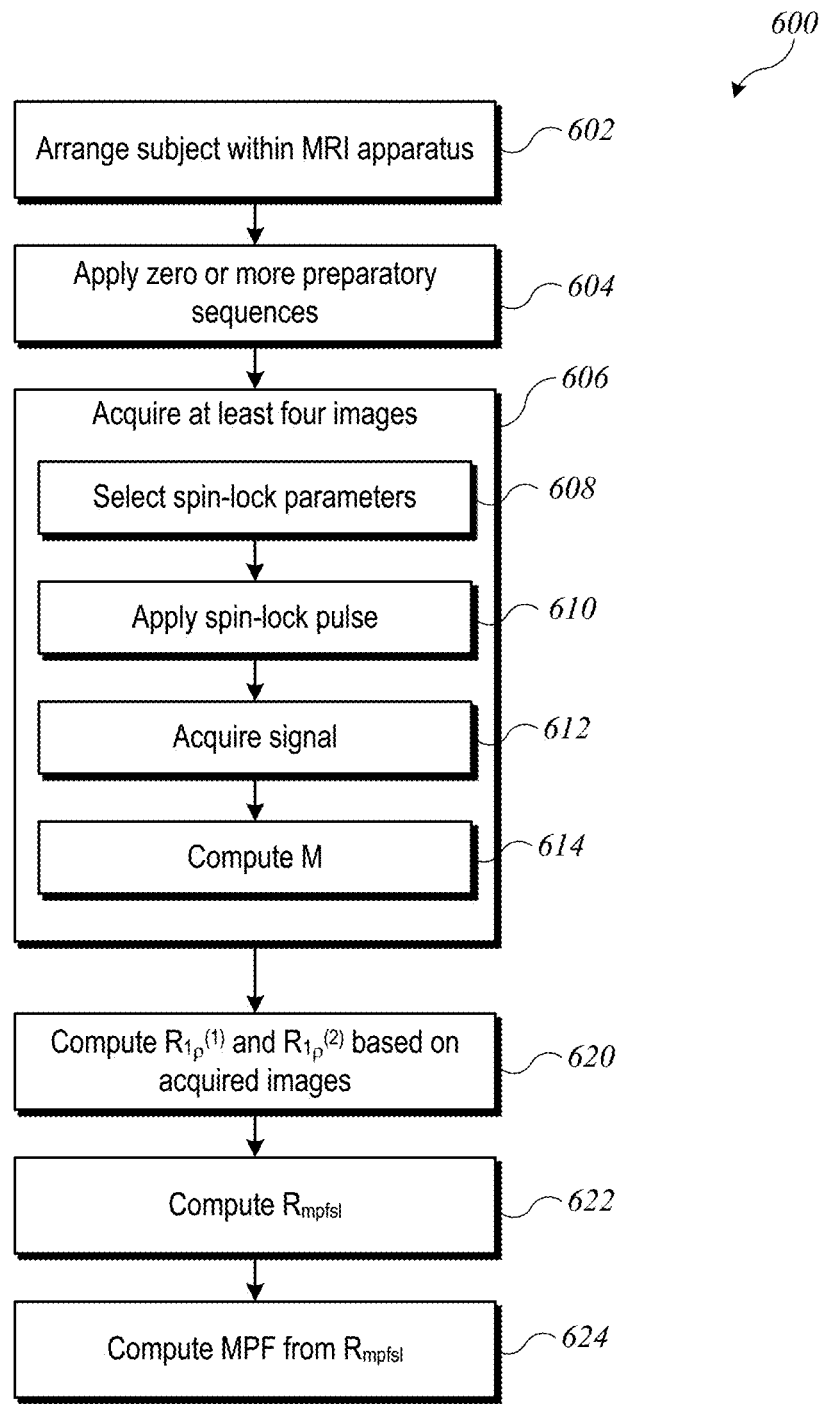
FIG. 6 shows a flow diagram of a third process 600 for determining MPF according to some embodiments.

FIG. 6 shows a flow diagram of a process 600 for determining MPF according to some embodiments. Process 600 can be performed using an MRI apparatus such as MRI apparatus 100 of FIG. 1. At block 602, a subject (e.g., a patient whose tissue is to be imaged) is arranged within an MRI apparatus. This can include having the patient assume a supine or other desired position and aligning the patient within the MRI apparatus. In some embodiments, this may also include positioning of RF and/or gradient coils; the particular positioning will depend on what is being imaged.

At block 604, various preparatory pulse sequences can be applied. Examples include magnetization reset sequences, sequences to reduce the effect of selected tissue types (e.g., blood, fat, etc.), and the like. Such sequences can be conventional and are optional; a detailed description is omitted as not being critical to understanding the claimed invention.

At block 606, at least four image acquisitions are performed. In some embodiments, each image acquisition i includes selecting characteristics for a spin-lock pulse (including a spin-lock RF pulse cluster or a saturation RF pulse) at block 608. The selected characteristics can include the duration of the spin-lock RF pulse or the saturation RF pulse $(TSL_i)$, B1 amplitude of the spin-lock RF pulse (spin-lock frequency) or the saturation RF pulse, and frequency offset. In some embodiments, half the acquisitions are performed using a first selection of $\omega_1^{(1)}$ and $\Delta\omega^{(1)}$ while the other half are performed using a second selection of $\omega_1^{(2)}$ and $\Delta\omega^{(2)}$ that satisfy the conditions of Eqs. (8)-(10), while $TSL_i$ is varied for different acquisitions such that different acquisitions i using the same selection of $(\omega_1^{(1)}, \Delta\omega^{(1)})$ or $(\omega_1^{(2)}, \Delta\omega^{(2)})$ use different $TSL_i$. At block 610, a spin-lock pulse having the selected characteristics is applied, followed by signal acquisition at block 612. Similarly to process 400 or process 500, signal acquisition can include generating RF pulses to stimulate a signal from the subject and operating an RF receiver coil to detect the signal. Various acquisition sequences can be performed, including single-shot or multi-shot fast spin echo (FSE) sequences; other acquisition sequences and techniques suitable for quantifying $R_{1\rho}$ can also be used. During the signal acquisition, a data set can be collected. At block 614, an image M can be computed based on the data set. Conventional techniques for generating images from acquired MRI data can be used; examples include Fourier transform of acquired k-space data. Blocks 608-614 can be repeated for each image that is to be acquired. The number of image acquisitions can be chosen as desired. At least four acquisitions are needed since there are four unknowns to be determined. Additional acquisitions may be performed if desired and may improve the optimization result.

At block 620, after acquiring the images, $R_{1\rho}^{(1)}$ and $R_{1\rho}^{(2)}$ can be computed based on the images, using optimization procedures as described above. At block 622 relaxation parameter) $R_{mpfsl}$ can be computed as $R_{mpfsl}=R_{1\rho}^{(2)}-R_{1\rho}^{(1)}$. At block 624, MPF can be computed from $R_{mpfsl}$, e.g., according to Eqs. (11) and (6).

Process 600 is illustrative, and variations or modifications are possible. For instance, acquisition of the images can occur in any order. Off-resonance frequencies and RF amplitudes for the spin-lock pulses (which can include a spin-lock RF pulse cluster or a saturation RF pulse) can be chosen as desired, subject to Eqs. (8)-(10). In some embodiments, crusher gradients can be applied after each spin-lock pulse and prior to each signal acquisition sequence. Fat suppression and/or other preparatory pulse sequences can be applied before or after each spin-lock pulse and prior to each signal acquisition sequence. Process 600 can be performed using as few as four acquisitions.

According to a fourth approach, $R_{mpfsl}$ can be determined by obtaining $R_{1\rho}^{(1)}$ and $R_{1\rho}^{(2)}$ individually, then computing the difference, again without knowledge of $R_{1obs}$ and $M_0$. In the fourth approach, the pulse sequence is designed such that:

$$M_{ini}=M_0-M_0 \cdot e^{-\tau 1 \cdot R_{1obs}} \quad (18)$$

where τ1 is a known time interval. Considering Eqs. (14'), (16'), and (18), there are again four unknowns: $R_{1\rho}^{(1)}$, $R_{1\rho}^{(2)}$, $M_0$ and $R_{1obs}$. Thus, as in the third approach, if at least two acquisitions i are performed using RF amplitude $\omega_1^{(1)}$ and frequency offset $\Delta\omega^{(1)}$ and at least two other acquisitions i are performed using RF amplitude $\omega_1^{(2)}$ and frequency offset $\Delta\omega^{(2)}$, with varying values of $TSL_i$, $R_{1\rho}^{(1)}$ and $R_{1\rho}^{(2)}$ can be derived from Eqs. (14'), (16'), and (18) using traditional optimization approaches, neural networks, or other optimization procedures. $R_{mpfsl}$ can be computed as $R_{mpfsl}=R_{1\rho}^{(2)}-R_{1\rho}^{(1)}$. Process 600 or a similar process can be used to implement the fourth approach as well as the third approach.

Processes described above or other similar processes can provide a quantitative measurement of MPF that is specific to the MT effect. As shown in Eq. (7), the subtraction process can remove $R_{water}$ and thus mitigate the influence of water content due to inflammation or other causes (e.g., iron in the liver). As noted above, these and other processes can use multiple images from which parameters $f_b$, $k_{ba}$, and $T_{2b}$ can all be determined by fitting to the measurements using Eq. (11).

Examples: Simulation Studies

Numerical simulations have been performed applying process 400 to tissues including cartilage, white matter (WM), and liver. Nominal values for relevant parameters were defined as shown in Table 2. The spin-lock parameters were chosen as: $\Delta\omega^{(1)}=2\pi \cdot 1000$ Hz, $\Delta\omega^{(2)}=2\pi \cdot 4000$ Hz, $\omega_1^{(1)}=2\pi \cdot 100$ Hz, $\omega_1^{(2)}=2\pi \cdot 400$ Hz. Following off-resonance spin-lock, a crusher gradient was applied to dephase magnetization in the transverse plane prior to data acquisition.

TABLE 2

| Tissue Type | $T_{1a}$ (ms) | $T_{2a}$ (ms) | $T_{1b}$ (ms) | $T_{2b}$ (us) | $k_{ba}$ ($S^{-1}$) | $f_b$ (%) |
|---|---|---|---|---|---|---|
| Cartilage | 1168 | 27 | 1168 | 8.3 | 57 | 17.1 |
| WM | 1084 | 69 | 1084 | 10 | 23 | 13.9 |
| Liver | 812 | 42 | 812 | 7.7 | 51 | 6.9 |

Figure 7:
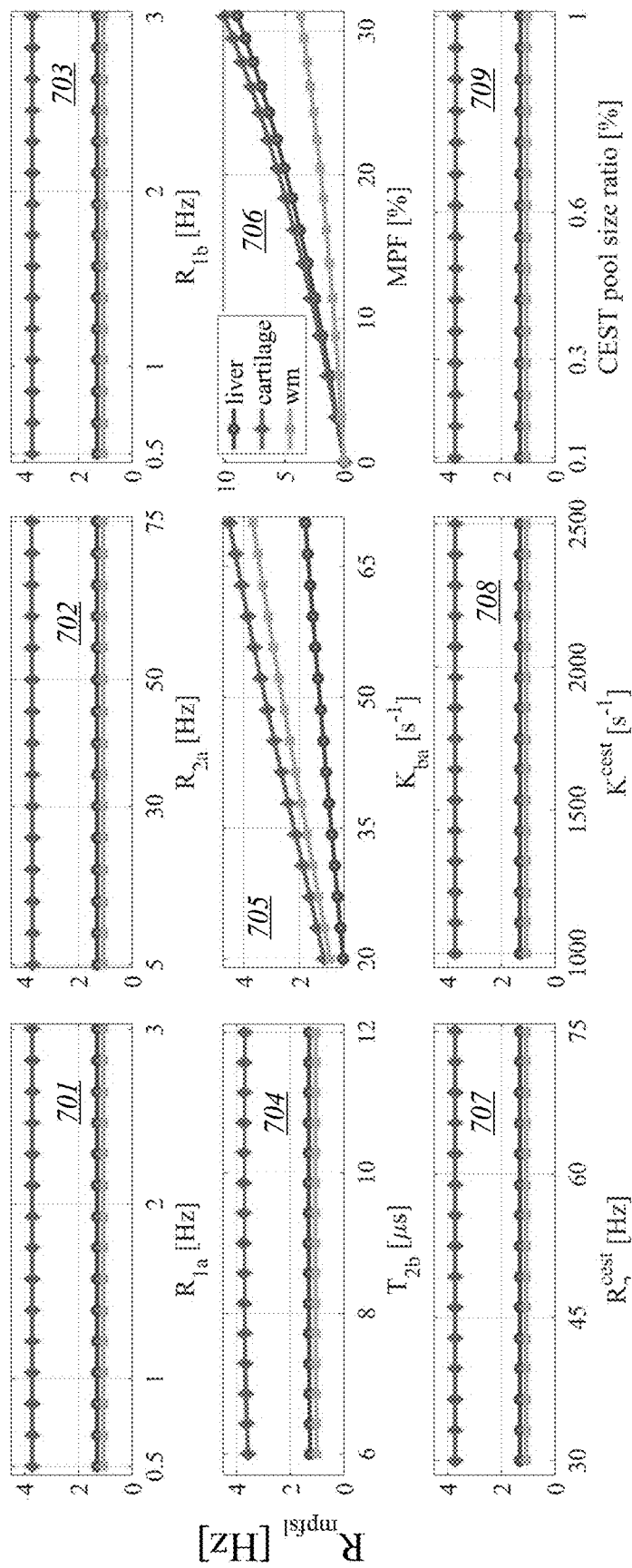
FIG. 7 shows simulation results according to some embodiments for different tissue types and for varying values of different parameters.

A first simulation study was performed to assess sensitivity of $R_{mprsl}$ to the presence of chemical exchange. Eq. (11) was derived based on a two-pool model including a free-water pool and a bound pool. It is recognized that a third pool is typically present in tissues, representing chemical exchange. To assess sensitivity of $R_{mprsl}$ to the presence of a chemical exchange (CEST) pool, simulations were carried out using a three-pool Bloch-McConnell simulation, with a free-water pool, CEST pool, and bound pool. For the CEST pool, the following parameters were used: $R_1^{cest}=R_{1a}$ (longitudinal relaxation rate of the free-water pool); $R_2^{cest}=67$ Hz; chemical shift $\Delta\omega_{cest}=1.9$ ppm; exchange rate from CEST pool to free-water pool $k^{cest}=1500$ $s^{-1}$; and CEST pool size ratio $f^{cest}=0.14\%$. For the free-water pool and the bound pool, parameters of Table 2 were used as nominal values. FIG. 7 shows simulation results for liver (blue circles), cartilage (red diamonds), and white matter (gold squares) for varying values of the following parameters: $R_{1a}$ (graph 701); $R_{2a}$ (graph 702); $R_{1b}$ (graph 703); $T_{2b}$ (graph 704); $k_{ba}$ (graph 705); MPF, which is a function of $f_b$ according to Eq. (6) (graph 706); $R_2^{cest}$ (graph 707); $k^{cest}$ (graph 708); and CEST pool size ratio $f^{cest}$ (graph 709). In each graph 701-709, $R_{mpfsl}$ is plotted as a function of the respective parameter over a range from half the nominal value of the parameter to twice the nominal value. For each tissue type, $R_{mpfsl}$ is sensitive to $f_b$ (MPF), $k_{ba}$, and $T_{2b}$, as predicted by Eq. (11), but is not sensitive to other parameters. It is noted that other work in the field has established that $R_{2b}$ ($=1/T_{2b}$) and $k_{ba}$ can be considered approximately constant in certain applications, which simplifies the process of determining MPF from $R_{mpfsl}$.

Figure 8:
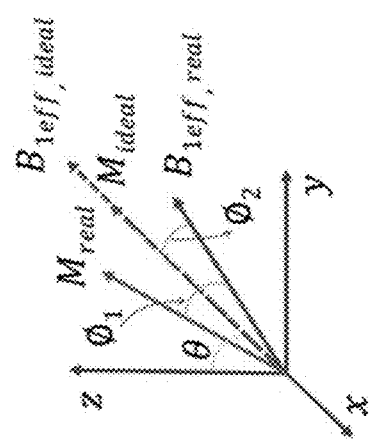
FIG. 8 shows an example of a mismatch between expected and actual spin-lock direction that can occur due to field inhomogeneities.

A second simulation study was performed to assess sensitivity of $R_{mpfsl}$ to B1 RF and B0 field inhomogeneities. Assuming the condition of Eq. (8) is satisfied, $\theta^{(1)}=\theta^{(2)}$, and the influence of the free-water pool is removed. However, the presence of B1 RF and B0 field inhomogeneities may result in $\theta^{(1)}\neq\theta^{(2)}$, resulting in calculation error. FIG. 8 shows an example of a mismatch between expected and actual spin-lock direction that can occur due to field inhomogeneities. In the ideal case, the direction of magnetization ($M_{ideal}$) aligns with the effective direction of spin-lock field ($B_{1eff, ideal}$) at an angle θ to the longitudinal (z) axis. In the presence of B1 RF and B0 field inhomogeneities, the actual effective direction of spin-lock field ($B_{1eff, real}$) deviates from the ideal direction by an angle $\phi_2$, and the direction of magnetization ($M_{real}$) deviates from the direction $B_{1eff}$, real by an angle $\phi_1$.

Figure 9A:
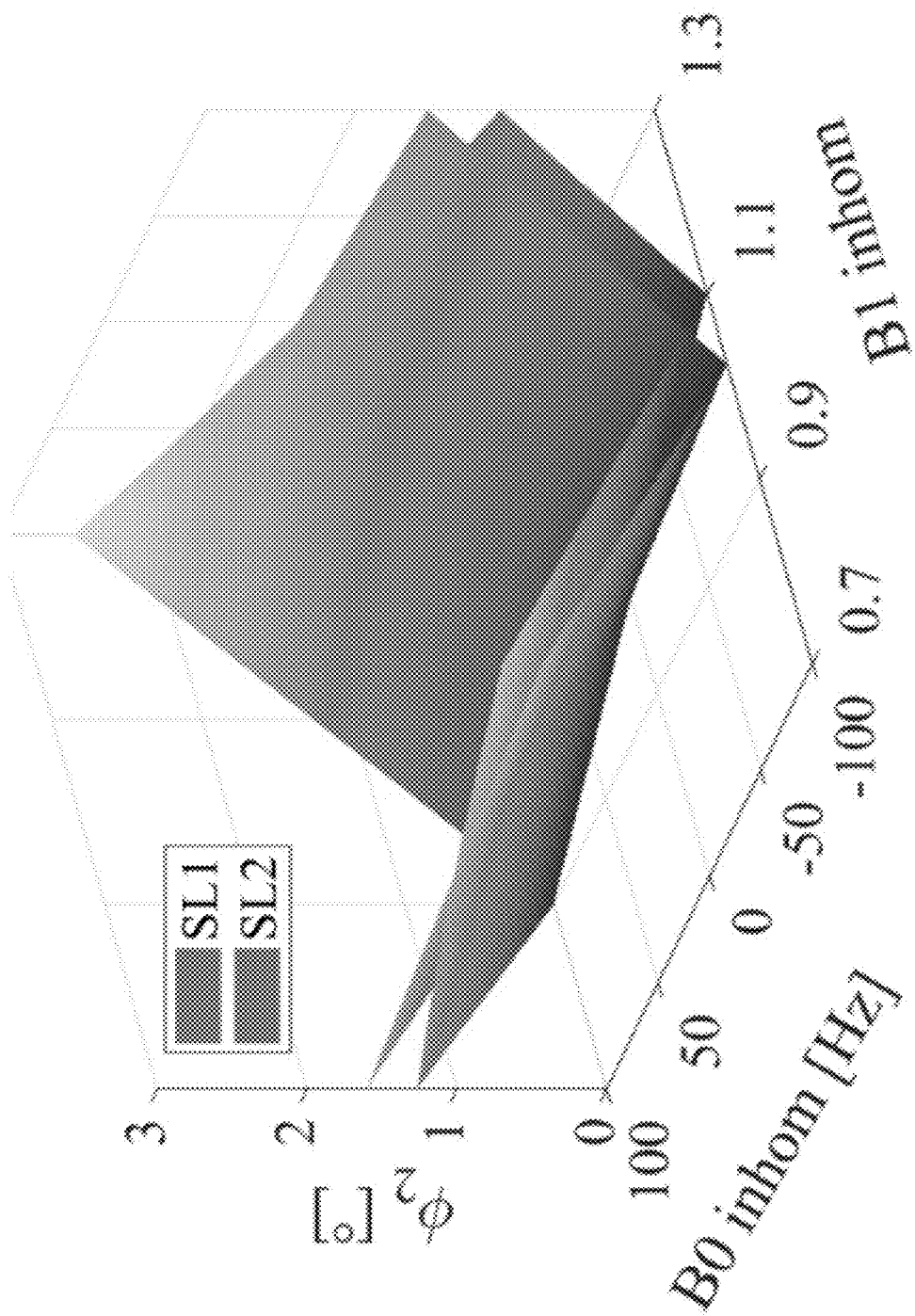
FIGS. 9A-9C show results of a simulation of the effect of varying amounts of field inhomogeneities on the deviation between expected and actual spin-lock field direction (FIG. 9A), the angle between actual spin-lock field direction and magnetization direction (FIG. 9B), and the relative error in measured MPF (FIG. 9C) according to some embodiments.
Figure 9B:
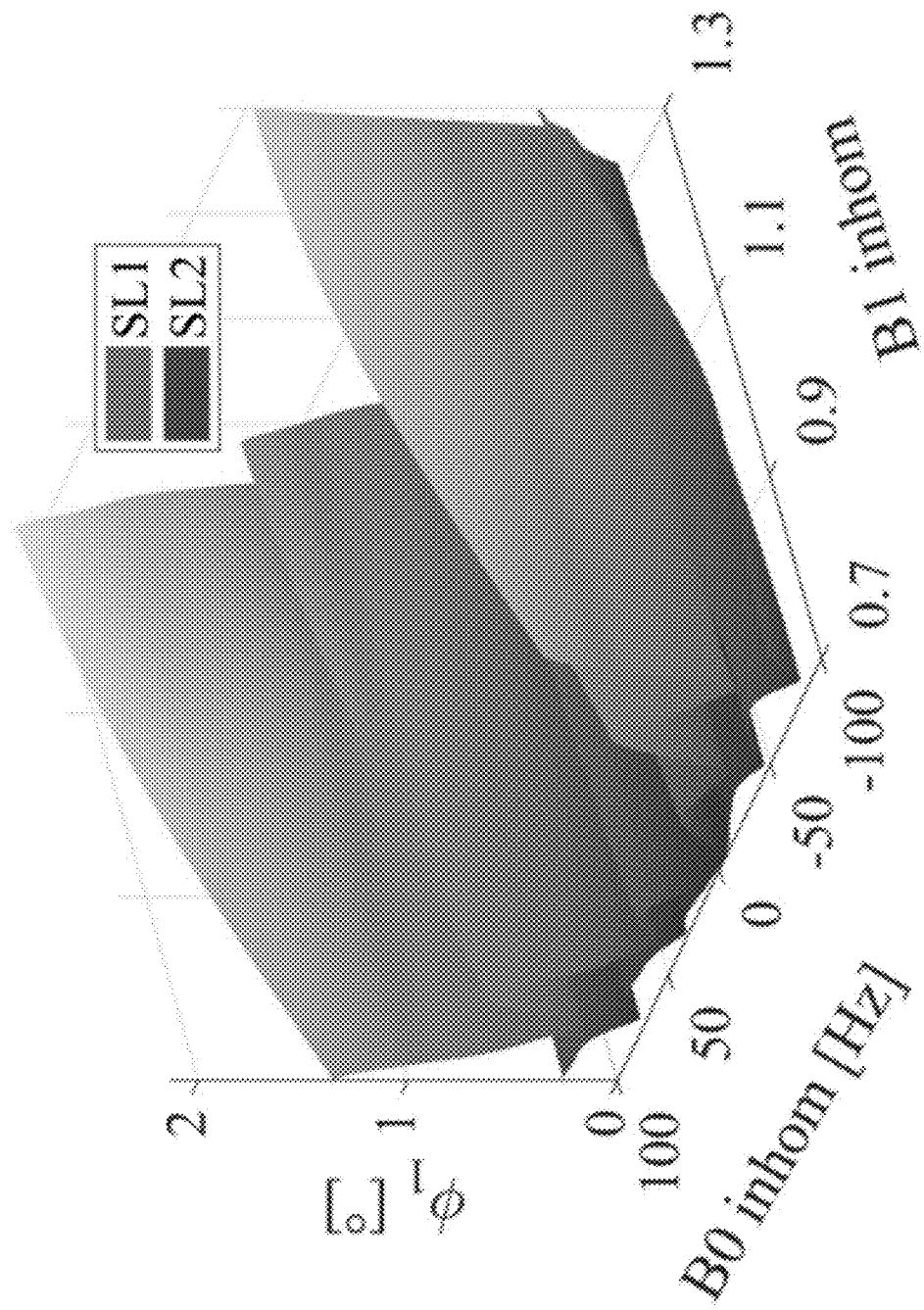
Figure 9C:
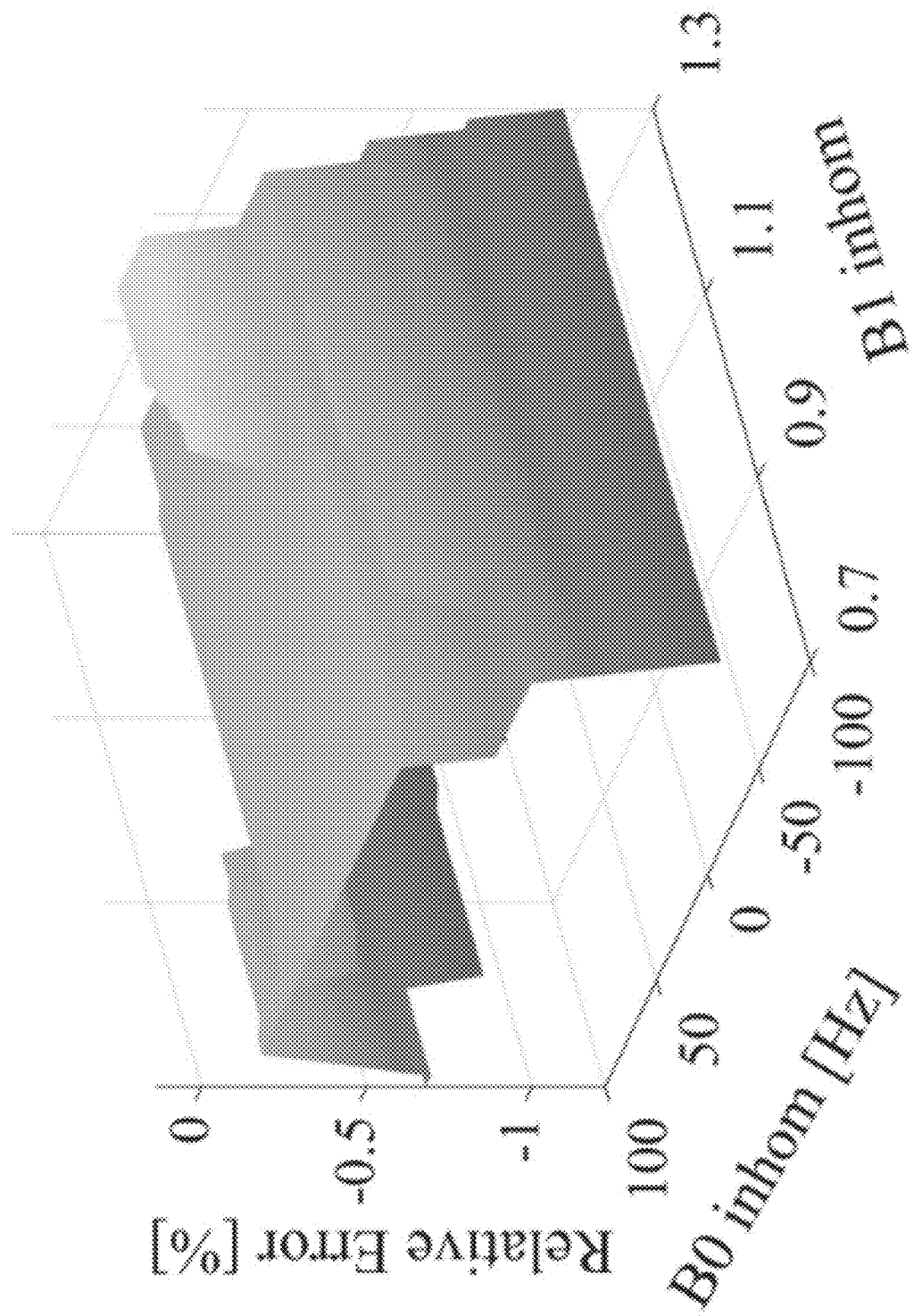

To assess the effect of field inhomogeneities, simulations were carried out using a two-pool Bloch-McConnell simulation, with a free-water pool and an MT pool, under varying conditions of B1 RF and B0 field inhomogeneities. Parameters for liver tissue were used. Under each set of conditions, determination of $R_{mpfsl}$ and MPF was performed using the first approach described above. FIGS. 9A-9C show results of the simulation. FIGS. 9A and 9B show the distribution of angles $\phi_2$ and $\phi_1$, respectively, as a function of inhomogeneity in B1 (range from 0.7 to 1.3) and B0 (range from 100 Hz to +100 Hz). FIG. 9C shows the relative error in the measured MPF as a function of inhomogeneity in B1 and B0. As can be seen, the errors were less than 1% within the simulated range of inhomogeneities. Simulations using other tissue types (cartilage and white matter) yield similarly low relative error.

Additional Embodiments

While the invention has been described with reference to specific embodiments, those skilled in the art will appreciate that numerous modifications are possible. For example, pulse sequence parameters described above can be modified, and additional pulse sequences can be incorporated as desired. Any of the above or other approaches can be used to determine $R_{mpfsl}$, as defined by Eq. (7), from MRI image data. MT quantification as described herein can be applied to a variety of tissue types, not limited to specific examples disclosed herein.

In some embodiments, image analysis operations as described above can be performed in the same computer system that performs image acquisition (e.g., as described with reference to FIG. 1). In other embodiments, distributed computing systems can be used, and image data acquired using an image acquisition system (e.g., as described above with reference to FIG. 1) can be transferred to a different computer system for analysis. It should be understood that a computer systems can include hardware components of generally conventional design (e.g., processors, memory and/or other storage devices, user interface components, network interface components) and that program code or other instructions can be provided to the computer system to cause the system to perform computations and/or other processes implementing embodiments described herein or aspects thereof.

Thus, although the invention has been described with respect to specific embodiments, it will be appreciated that the invention is intended to cover all modifications and equivalents within the scope of the following claims.

What is claimed is:

1. A method for quantifying magnetization transfer using a magnetic resonance imaging (MRI) apparatus, the method comprising:
performing a plurality of image acquisition processes to produce a plurality of MRI images, wherein each image acquisition process (i) in the plurality of image acquisition process includes applying an off-resonance spin-lock pulse having an RF amplitude ($\omega_1^{(i)}$) and a frequency offset ($\Delta\omega^{(i)}$); and
computing, based on the plurality of MRI images one or more parameters of magnetization transfer, wherein the one or more parameters of magnetization transfer include a parameter $R_{mpfsl}$ defined as $R_{mpfsl} = R_{1\rho}^{(2)} - R_{1\rho}^{(1)}$, wherein:
$R_{1\rho}^{(1)}$ is a first relaxation rate in a rotating frame responsive to a spin-lock pulse having a first RF amplitude $\omega_1^{(1)}$ and a first frequency offset $\Delta\omega^{(1)}$;
$R_{1\rho}^{(2)}$ is a second relaxation rate in the rotating frame responsive to a spin-lock pulse having a second RF amplitude $\omega_1^{(2)}$ and a second frequency offset $\Delta\omega^{(2)}$;
the first RF amplitude $\omega_1^{(1)}$ is different from the second RF amplitude $\omega_1^{(2)}$; and the first RF amplitude $\omega_1^{(1)}$, the first frequency offset $\Delta\omega^{(1)}$, the second RF amplitude $\omega_1^{(2)}$, and the second frequency offset $\Delta\omega^{(2)}$ are chosen such that $\Delta\omega^{(1)}/\omega_1^{(1)} = \Delta\omega^{(2)}/\omega_1^{(2)}$.

2. The method of claim 1 further comprising:
computing one or more additional parameters of magnetization transfer based on the parameter $R_{mpfsl}$.

3. The method of claim 2 wherein the one or more additional parameters of magnetization transfer includes a pool size ratio ($f_b$) of a bound pool of protons bound to semi-solid macromolecules that is computed from the parameter $R_{mpfsl}$ according to the equation $$R_{mpfsl} = k_{ba}^2 f_b (1+f_b) \left( \frac{1}{(1+f_b)k_{ba} + R_{rfc}^{(1)}} - \frac{1}{(1+f_b)k_{ba} + R_{rfc}^{(2)}} \right),$$

wherein $k_{ba}$ is a magnetization exchange rate between a free-water pool and the bound pool, $R_{rfc}^{(1)}$ is a parameter representing a saturation rate of the bound pool at the first off-resonance frequency $\Delta\omega^{(1)}$ and the first RF amplitude $\omega_1^{(1)}$, $R_{rfc}^{(2)}$ is a parameter representing a saturation rate of the bound pool at the second off-resonance frequency $\Delta\omega^{(2)}$ and the second RF amplitude $\omega_1^{(2)}$.

4. The method of claim 3 wherein the saturation rate parameter $R_{rfc}$ is a function of RF amplitude ($\omega_1$), off-resonance frequency ($\Delta\omega$), and a transverse relaxation time of the bound pool ($T_{2b}$).

5. The method of claim 4 wherein the magnetization exchange rate $k_{ba}$ and the transverse relaxation time of the bound pool $T_{2b}$ are treated as constants that do not depend on the off-resonance frequency $\Delta\omega$ or the RF amplitude $\omega_1$.

6. The method of claim 4 wherein the magnetization exchange rate $k_{ba}$ and the transverse relaxation time of the bound pool $T_{2b}$ are treated as variables that are determined by fitting to the plurality of MRI images.

7. The method of claim 2 wherein the one or more additional parameters of magnetization transfer include a macromolecular proton fraction (MPF) indicating a fraction of protons that are bound to semi-solid macromolecules.

8. The method of claim 1 wherein performing the plurality of image acquisition processes includes:
performing a first image acquisition process using a first spin-lock pulse at the first RF amplitude $\omega_1^{(1)}$ and the first frequency offset $\Delta\omega^{(1)}$ without a toggling RF pulse, wherein the first image acquisition process produces a first MRI image ($M_{noTog}^{(1)}$);
performing a second image acquisition process using a second spin-lock pulse at the first RF amplitude $\omega_1^{(1)}$ and the first frequency offset $\Delta\omega^{(1)}$ with a toggling RF pulse, wherein the second image acquisition process produces a second MRI image ($M_{Tog}^{(1)}$);
performing a third image acquisition process using a third spin-lock pulse at the second RF amplitude $\omega_1^{(2)}$ and the second frequency offset $\Delta\omega^{(2)}$ without a toggling RF pulse, wherein the third image acquisition process produces a third MRI image ($M_{noTog}^{(2)}$); and
performing a fourth image acquisition process using a fourth spin-lock pulse at the second RF amplitude $\omega_1^{(2)}$ and the second frequency offset $\Delta\omega^{(2)}$ with a toggling RF pulse, wherein the fourth image acquisition process produces a fourth MRI image $M_{Tog}^{(2)}$).

9. The method of claim 8 wherein a same time of spin-lock (TSL) is used for each of the first, second, third, and fourth spin-lock pulses and wherein the parameter $R_{mpfsl}$ is measured according to the equation:

$$R_{mpfsl} = -\log\left(\frac{M_{Tog}^{(2)} - M_{noTog}^{(2)}}{M_{Tog}^{(1)} - M_{noTog}^{(1)}}\right)/TSL.$$

10. The method of claim 1 wherein:
performing the plurality of image acquisition processes includes:
  performing a first image acquisition process using a first spin-lock pulse at the first RF amplitude $\omega_1^{(1)}$ and the first frequency offset $\Delta\omega^{(1)}$ with a spin-lock time of zero to determine a first magnetization value;
  performing a second image acquisition process using a second spin-lock pulse at the first RF amplitude $\omega_1^{(1)}$ and the first frequency offset $\Delta\omega^{(1)}$ with a spin-lock time greater than zero to determine a second magnetization value;
  performing a third image acquisition process using a third spin-lock pulse at the second RF amplitude $\omega_1^{(2)}$ and the second frequency offset $\Delta\omega^{(2)}$ with a spin-lock time greater than zero to determine a third magnetization value; and
computing the parameter $R_{mpfsl}$ includes:
  computing the first relaxation rate $R_{1\rho}^{(1)}$ based on the first magnetization value and the second magnetization value; and
  computing the second relaxation rate $R_{1\rho}^{(2)}$ based on the first magnetization value and the third magnetization value.

11. The method of claim 10 further comprising:
performing one or more additional image acquisition processes to measure an observed longitudinal relaxation rate ($R_{1obs}$) and an equilibrium magnetization ($M_0$) or the product $R_{1obs}\cdot M_0$,
wherein the observed longitudinal relaxation rate $R_{1obs}$ and the equilibrium magnetization $M_0$ or the product $R_{1obs}\cdot M_0$ are used in computing the first relaxation rate $R_{1\rho}^{(1)}$ and the second relaxation rate $R_{1\rho}^{(2)}$.

12. The method of claim 1 wherein:
each image acquisition process in a first subset of the plurality of image acquisition processes includes applying a spin-lock pulse having the first RF amplitude $\omega_1^{(1)}$ and the first frequency offset $\Delta\omega^{(1)}$; and
each image acquisition process in a second subset of the plurality of image acquisition processes includes applying a spin-lock pulse having the second RF amplitude $\omega_1^{(2)}$ and the second frequency offset $\Delta\omega^{(2)}$.

13. The method of claim 12 wherein:
the first subset of the plurality of the image acquisition processes and the second subset of the plurality of image acquisition processes each include at least two image acquisition processes;
each image acquisition process in the first subset uses a spin-lock pulse having a time of spin-lock (TSL) that is different from the TSL of each other image acquisition process in the first subset;
each image acquisition process in the second subset uses a spin-lock pulse having a TSL that is different from the TSL of each other image acquisition process in the second subset; and
the first relaxation rate $R_{1\rho}^{(1)}$ and the second relaxation rate $R_{1\rho}^{(2)}$ are computed from the plurality of images.

14. The method of claim 13 wherein each image acquisition process includes determining a measured magnetization and wherein the first relaxation rate $R_{1\rho}^{(1)}$ and the second relaxation rate $R_{1\rho}^{(2)}$ are computed from the plurality of images by optimization of the equations:

$$M_i^{(1)} = M_{ini}\cdot e^{-R_{1\rho}^{(1)}\cdot TSL_i^{(1)}} + \frac{\cos\theta\cdot R_{1obs}}{R_{1\rho}^{(1)}}\cdot M_0\cdot\left(1 - e^{-R_{1\rho}^{(1)}\cdot TSL_i^{(1)}}\right) \text{ and}$$

$$M_i^{(2)} = M_{ini}\cdot e^{-R_{1\rho}^{(2)}\cdot TSL_i^{(2)}} + \frac{\cos\theta\cdot R_{1obs}}{R_{1\rho}^{(2)}}\cdot M_0\cdot\left(1 - e^{-R_{1\rho}^{(2)}\cdot TSL_i^{(2)}}\right)$$

for variables $R_{1\rho}^{(1)}$, $R_{1\rho}^{(2)}$, $M_{ini}$ and $M_0\cdot R_{1obs}$,
wherein:
  $M_0\cdot R_{1obs}$ is a product of a longitudinal relaxation rate ($R_{1obs}$) and an equilibrium magnetization ($M_0$);
  $\theta$ is equal to $\tan^{-1}(\omega_1^{(1)}/\Delta\omega^{(1)})$;
  $TSL_i^{(1)}$ and $M_i^{(1)}$ are the time of spin-lock and the measured magnetization from the ith image acquisition process in the first subset;
  $TSL_i^{(2)}$ and $M_i^{(2)}$ are the time of spin-lock and the measured magnetization from the ith image acquisition process in the second subset; and
  $M_{ini}$ is an initial magnetization at the beginning of spin-lock.

15. The method of claim 13 wherein performing the plurality of image acquisition processes includes:
for each of the plurality of image acquisition processes, using a pulse sequence such that:

$$M_{ini} = M_0 - M_0\cdot e^{-\tau 1\cdot R_{1obs}},$$

wherein $M_{ini}$ is an initial magnetization at the beginning of spin-lock, $\tau 1$ is a known time interval, $M_0$ is an equilibrium magnetization, and $R_{1obs}$ is a longitudinal relaxation rate.

16. The method of claim 15 wherein each image acquisition process includes determining a measured magnetization and wherein the first relaxation rate $R_{1\rho}^{(1)}$ and the second relaxation rate $R_{1\rho}^{(2)}$ are computed from the plurality of images by optimization of the equations:

$$M_i^{(1)} = M_{ini}\cdot e^{-R_{1\rho}^{(1)}\cdot TSL_i^{(1)}} + \frac{\cos\theta\cdot R_{1obs}}{R_{1\rho}^{(1)}}\cdot M_0\cdot\left(1 - e^{-R_{1\rho}^{(1)}\cdot TSL_i^{(1)}}\right) \text{ and}$$

$$M_i^{(2)} = M_{ini}\cdot e^{-R_{1\rho}^{(2)}\cdot TSL_i^{(2)}} + \frac{\cos\theta\cdot R_{1obs}}{R_{1\rho}^{(2)}}\cdot M_0\cdot\left(1 - e^{-R_{1\rho}^{(2)}\cdot TSL_i^{(2)}}\right)$$

for variables $R_{1\rho}^{(1)}$, $R_{1\rho}^{(2)}$, $M_0$ and $R_{1obs}$,
wherein:
  $\theta$ is equal to $\tan^{-1}(\omega_1^{(1)}/\Delta\omega^{(1)})$;
  $TSL_i^{(1)}$ and $M_i^{(1)}$ are the time of spin-lock and the measured magnetization from the ith image acquisition process in the first subset; and
  $TSL_i^{(2)}$ and $M_i^{(2)}$ are the time of spin-lock and the measured magnetization from the ith image acquisition process in the second subset.

17. The method of claim 1 wherein each instance of applying an off-resonance spin-lock pulse includes applying an off-resonance spin-lock RF pulse cluster.

18. The method of claim 1 wherein each instance of applying an off-resonance spin-lock pulse includes applying a saturation RF pulse.

19. The method of claim 1 wherein performing each of the plurality of image acquisition processes includes applying at least one preparatory pulse sequence before or after applying the spin-lock pulse and prior to acquiring data.

20. The method of claim 1 wherein the MRI images comprise images of a tissue of a patient.

21. A magnetic resonance imaging (MRI) system comprising:
an MRI apparatus having a magnet, a gradient coil, and one or more radiofrequency (RF) coils; and
a computer communicably coupled to the MRI apparatus, the computer having a processor, a memory, and a user interface, the processor being configured to:
perform a plurality of image acquisition processes using the MRI apparatus to produce a plurality of MRI images, wherein each image acquisition process (i) in the plurality of image acquisition process includes applying an off-resonance spin-lock pulse having an RF amplitude ($\omega_1^{(i)}$) and a frequency offset ($\Delta\omega^{(i)}$); and
compute, based on the plurality of MRI images, one or more parameters of magnetization transfer, wherein the one or more parameters of magnetization transfer include a parameter $R_{mpfsl}$ defined as $R_{mpfsl} = R_{1\rho}^{(2)} - R_{1\rho}^{(1)}$, wherein:
$R_{1\rho}^{(1)}$ is a first relaxation rate in a rotating frame responsive to a spin-lock pulse having a first RF amplitude $\omega_1^{(1)}$ and a first frequency offset $\Delta\omega^{(1)}$;
$R_{1\rho}^{(2)}$ is a second relaxation rate in the rotating frame responsive to a spin-lock pulse having a second RF amplitude $\omega_1^{(2)}$ and a second frequency offset $\Delta\omega^{(2)}$;
the first RF amplitude $\omega_1^{(1)}$ is different from the second RF amplitude $\omega_1^{(2)}$; and
the first RF amplitude $\omega_1^{(1)}$, the first frequency offset $\Delta\omega^{(1)}$, the second RF amplitude $\omega_1^{(2)}$, and the second frequency offset $\Delta\omega^{(2)}$ are chosen such that $\Delta\omega^{(1)}/\omega_1^{(1)} = \Delta\omega^{(2)}/\omega_1^{(2)}$.

22. The system of claim 21 wherein the processor is further configured to compute one or more additional parameters of magnetization transfer based on the parameter $R_{mpfsl}$.

23. The system of claim 22 wherein:
the one or more additional parameters of magnetization transfer includes a pool size ratio ($f_b$) of a bound pool of protons bound to semi-solid macromolecules that is computed from the parameter $R_{mpfsl}$ according to the equation $$R_{mpfsl} = k_{ba}^2 f_b (1 + f_b) \left( \frac{1}{(1+f_b)k_{ba} + R_{rfc}^{(1)}} - \frac{1}{(1+f_b)k_{ba} + R_{rfc}^{(2)}} \right),$$

wherein $k_{ba}$ is a magnetization exchange rate between a free-water pool and the bound pool, $R_{rfc}^{(1)}$ is a parameter representing a saturation rate of the bound pool at the first off-resonance frequency $\Delta\omega^{(1)}$ and the first RF amplitude $\omega_1^{(1)}$, and $R_{rfc}^{(2)}$ is a parameter representing a saturation rate of the bound pool at the second off-resonance frequency $\Delta\omega^{(2)}$ and the second RF amplitude $\omega_1^{(2)}$.

24. The system of claim 23 wherein the saturation rate parameter $R_{rfc}$ is a function of the RF amplitude ($\omega_1$), the off-resonance frequency ($\Delta\omega$), and the transverse relaxation time of the bound pool ($T_{2b}$).

25. The system of claim 24 wherein the processor is further configured such that the magnetization exchange rate $k_{ba}$ and the transverse relaxation time of the bound pool $T_{2b}$ are treated as constants that do not depend on the off-resonance frequency $\Delta\omega$ or the RF amplitude $\omega_1$.

26. The system of claim 24 wherein the processor is further configured such that the magnetization exchange rate $k_{ba}$ and the transverse relaxation time of the bound pool $T_{2b}$ are treated as variables that are determined by fitting to the plurality of MRI images.

27. The system of claim 22 wherein the one or more additional parameters of magnetization transfer include a macromolecular proton fraction (MPF) indicating a fraction of protons that are bound to semi-solid macromolecules.

28. The system of claim 21 wherein the processor is further configured such that performing the plurality of image acquisition processes includes:
performing a first image acquisition process using a first spin-lock pulse at the first RF amplitude $\omega_1^{(1)}$ and the first frequency offset $\Delta\omega^{(1)}$ without a toggling RF pulse, wherein the first image acquisition process produces a first MRI image ($M_{noTog}^{(1)}$);
performing a second image acquisition process using a second spin-lock pulse at the first RF amplitude $\omega_1^{(1)}$ and the first frequency offset $\Delta\omega^{(1)}$ with a toggling RF pulse, wherein the second image acquisition process produces a second MRI image ($M_{Tog}^{(1)}$);
performing a third image acquisition process using a third spin-lock pulse at the second RF amplitude $\omega_1^{(2)}$ and the second frequency offset $\Delta\omega^{(2)}$ without a toggling RF pulse, wherein the third image acquisition process produces a third MRI image ($M_{noTog}^{(2)}$); and
performing a fourth image acquisition process using a fourth spin-lock pulse at the second RF amplitude $\omega_1^{(2)}$ and the second frequency offset $\Delta\omega^{(2)}$ with a toggling RF pulse, wherein the fourth image acquisition process produces a fourth MRI image ($M_{Tog}^{(2)}$).

29. The system of claim 28 wherein the processor is further configured such that a same time of spin-lock (TSL) is used for each of the first, second, third, and fourth spin-lock pulses and such that the parameter $R_{mpfsl}$ is measured according to the equation:

$$R_{mpfsl} = -\log\left(\frac{M_{Tog}^{(2)} - M_{noTog}^{(2)}}{M_{Tog}^{(1)} - M_{noTog}^{(1)}}\right)/TSL.$$

30. The system of claim 21 wherein the processor is further configured such that:
performing the plurality of image acquisition processes includes:
performing a first image acquisition process using a first spin-lock pulse at the first RF amplitude $\omega_1^{(1)}$ and the first frequency offset $\Delta\omega^{(1)}$ with a spin-lock time of zero to determine a first magnetization value;
performing a second image acquisition process using a second spin-lock pulse at the first RF amplitude $\omega_1^{(1)}$ and the first frequency offset $\Delta\omega^{(1)}$ with a spin-lock time greater than zero to determine a second magnetization value;
performing a third image acquisition process using a third spin-lock pulse at the second RF amplitude $\omega_1^{(2)}$ and the second frequency offset $\Delta\omega^{(2)}$ with a spin-lock time greater than zero to determine a third magnetization value; and
computing the parameter $R_{mpfsl}$ includes:
computing the first relaxation rate $R_{1\rho}^{(1)}$ based on the first magnetization value and the second magnetization value; and computing the second relaxation rate $R_{1\rho}^{(2)}$ based on the first magnetization value and the third magnetization value.

31. The system of claim 30 wherein the processor is further configured to:
perform one or more additional image acquisition processes to measure an observed longitudinal relaxation rate ($R_{1obs}$) and an equilibrium magnetization $M_0$ or the product $R_{1obs} \cdot M_0$,
wherein the observed longitudinal relaxation rate $R_{1obs}$ and the equilibrium magnetization $M_0$ or the product $R_{1obs} \cdot M_0$ are used in computing the first relaxation rate $R_{1\rho}^{(1)}$ and the second relaxation rate $R_{1\rho}^{(2)}$.

32. The system of claim 21 wherein the processor is further configured such that:
each image acquisition process in a first subset of the plurality of image acquisition processes includes applying a spin-lock pulse having the first RF amplitude $\omega_1^{(1)}$ and the first frequency offset $\Delta\omega^{(1)}$; and
each image acquisition process in a second subset of the plurality of image acquisition processes includes applying a spin-lock pulse having the second RF amplitude $\omega_1^{(2)}$ and the second frequency offset $\Delta\omega^{(2)}$.

33. The system of claim 32 wherein the processor is further configured such that:
the first subset of the plurality of the image acquisition processes and the second subset of the plurality of image acquisition processes each include at least two image acquisition processes;
each image acquisition process in the first subset uses a spin-lock pulse having a time of spin-lock (TSL) that is different from the TSL of each other image acquisition process in the first subset;
each image acquisition process in the second subset uses a spin-lock pulse having a TSL that is different from the TSL of each other image acquisition process in the second subset; and
the first relaxation rate $R_{1\rho}^{(1)}$ and the second relaxation rate $R_{1\rho}^{(2)}$ are computed from the plurality of images.

34. The system of claim 33 wherein the processor is further configured such that each image acquisition process includes determining a measured magnetization and such that the first relaxation rate $R_{1\rho}^{(1)}$ and the second relaxation rate $R_{1\rho}^{(2)}$ are computed from the plurality of images by optimization of the equations:

$$M_i^{(1)} = M_{ini} \cdot e^{-R_{1\rho}^{(1)} \cdot TSL_i^{(1)}} + \frac{\cos\theta \cdot R_{1obs}}{R_{1\rho}^{(1)}} \cdot M_0 \cdot \left(1 - e^{-R_{1\rho}^{(1)} \cdot TSL_i^{(1)}}\right) \text{ and}$$

$$M_i^{(2)} = M_{ini} \cdot e^{-R_{1\rho}^{(2)} \cdot TSL_i^{(2)}} + \frac{\cos\theta \cdot R_{1obs}}{R_{1\rho}^{(2)}} \cdot M_0 \cdot \left(1 - e^{-R_{1\rho}^{(2)} \cdot TSL_i^{(2)}}\right)$$

for variables $R_{1\rho}^{(1)}$, $R_{1\rho}^{(2)}$, $M_{ini}$ and $M_0 \cdot R_{1obs}$,
wherein:
$M_0 \cdot R_{1obs}$ is a product of a longitudinal relaxation rate ($R_{1obs}$) and an equilibrium magnetization ($M_0$);
$\theta$ is equal to $\tan^{-1}(\omega_1^{(1)}/\Delta\omega^{(1)})$;
$TSL_i^{(1)}$ and $M_i^{(1)}$ are the time of spin-lock and the measured magnetization from the ith image acquisition process in the first subset;
$TSL_i^{(2)}$ and $M_i^{(2)}$ are the time of spin-lock and the measured magnetization from the ith image acquisition process in the second subset; and
$M_{ini}$ is an initial magnetization at the beginning of spin-lock.

35. The system of claim 33 wherein the processor is further configured such that performing the plurality of image acquisition processes includes:
for each of the plurality of image acquisition processes, using a pulse sequence such that:

$$M_{ini} = M_0 - M_0 \cdot e^{-\tau 1 \cdot R_{1obs}},$$

wherein $M_{ini}$ is an initial magnetization at the beginning of spin-lock, $\tau 1$ is a known time interval, $M_0$ is an equilibrium magnetization, and $R_{1obs}$ is a longitudinal relaxation rate.

36. The system of claim 35 wherein the processor is further configured such that each image acquisition process includes determining a measured magnetization and such that the first relaxation rate $R_{1\rho}^{(1)}$ and the second relaxation rate $R_{1\rho}^{(2)}$ are computed from the plurality of images by optimization of the equations:

$$M_i^{(1)} = M_{ini} \cdot e^{-R_{1\rho}^{(1)} \cdot TSL_i^{(1)}} + \frac{\cos\theta \cdot R_{1obs}}{R_{1\rho}^{(1)}} \cdot M_0 \cdot \left(1 - e^{-R_{1\rho}^{(1)} \cdot TSL_i^{(1)}}\right) \text{ and}$$

$$M_i^{(2)} = M_{ini} \cdot e^{-R_{1\rho}^{(2)} \cdot TSL_i^{(2)}} + \frac{\cos\theta \cdot R_{1obs}}{R_{1\rho}^{(2)}} \cdot M_0 \cdot \left(1 - e^{-R_{1\rho}^{(2)} \cdot TSL_i^{(2)}}\right)$$

for variables $R_{1\rho}^{(1)}$, $R_{1\rho}^{(2)}$, $M_0$ and $R_{1obs}$,
wherein:
$\theta$ is equal to $\tan^{-1}(\omega_1^{(1)}/\Delta\omega^{(1)})$;
$TSL_i^{(1)}$ and $M_i^{(1)}$ are the time of spin-lock and the measured magnetization from the ith image acquisition process in the first subset; and
$TSL_i^{(2)}$ and $M_i^{(2)}$ are the time of spin-lock and the measured magnetization from the ith image acquisition process in the second subset.

37. The system of claim 21 wherein each instance of applying an off-resonance spin-lock pulse includes applying an off-resonance spin-lock RF pulse cluster.

38. The system of claim 21 wherein each instance of applying an off-resonance spin-lock pulse includes applying a saturation RF pulse.

39. The system of claim 21 wherein the processor is further configured such that performing each of the plurality of image acquisition processes includes applying at least one preparatory pulse sequence before or after applying the spin-lock pulse and prior to acquiring data.

40. The system of claim 21 wherein the MRI images comprise images of a tissue of a patient.

* * * * *